(12) United States Patent
Chan et al.

(10) Patent No.: US 10,463,304 B2
(45) Date of Patent: Nov. 5, 2019

(54) INTEGRATED MULTIMODAL SENSOR DEVICE FOR INTRACRANIAL NEUROMONITORING

(71) Applicants: AGENCY FOR SCIENCE, TECHNOLOGY AND RESEARCH, Singapore (SG); SINGAPORE HEALTH SERVICES PTE. LTD., Singapore (SG)

(72) Inventors: Wai Pan Chan, Singapore (SG); Margarita Sofia Narducci, Singapore (SG); Yuan Gao, Singapore (SG); Julius Ming Lin Tsai, Singapore (SG); Ruiqi Lim, Singapore (SG); Ming-Yuan Cheng, Singapore (SG); Abdur Rub Abdur Rahman, Singapore (SG); Mi Kyoung Park, Singapore (SG); Minkyu Je, Singapore (SG); Jai Prashanth Rao, Singapore (SG)

(73) Assignees: AGENCY FOR SCIENCE, TECHNOLOGY AND RESEARCH, Singapore (SG); SINGAPORE HEALTH SERVICES PTE. LTD., Singapore (SG)

( * ) Notice: Subject to any disclaimer, the term of this patent is extended or adjusted under 35 U.S.C. 154(b) by 846 days.

(21) Appl. No.: 14/897,578

(22) PCT Filed: Jun. 12, 2014

(86) PCT No.: PCT/SG2014/000274
§ 371 (c)(1),
(2) Date: Dec. 10, 2015

(87) PCT Pub. No.: WO2014/200436
PCT Pub. Date: Dec. 18, 2014

(65) Prior Publication Data
US 2016/0135749 A1    May 19, 2016

(30) Foreign Application Priority Data

Jun. 12, 2013  (SG) ................................. 201304550

(51) Int. Cl.
*A61B 5/00* (2006.01)
*A61B 5/01* (2006.01)
(Continued)

(52) U.S. Cl.
CPC .......... *A61B 5/6852* (2013.01); *A61B 5/0008* (2013.01); *A61B 5/0031* (2013.01);
(Continued)

(58) Field of Classification Search
CPC combination set(s) only.
See application file for complete search history.

(56) References Cited

U.S. PATENT DOCUMENTS 6,533,733 B1 * 3/2003 Ericson ................ A61B 5/0031
                                                                  128/903
6,673,022 B1 * 1/2004 Bobo ...................... A61B 5/031
                                                                  600/561
(Continued)

OTHER PUBLICATIONS

Monolithically Integrated Multimodal Sensors and Their Readout IC's for Intracranial Neuro Monitoring by Wai Pan Chan ; Margarita Narducci ; Yuan Gao ; J T Ming Lin; Min-Yuan Cheng; A R A Rahman; P M Kyoung; M Je; J p. Rao; IEEE Journal of Solid-State Circuits ( vol. 49 , Issue: 11 , Nov. 2014 ).
(Continued)

*Primary Examiner* — Christopher A Flory
*Assistant Examiner* — Shirley X Jian
(74) *Attorney, Agent, or Firm* — Womble Bond Dickinson (US) LLP

(57) ABSTRACT

There is provided a monolithically integrated multimodal sensor device for intracranial neuromonitoring, the sensor device including: a single substrate; a temperature sensor
(Continued)

formed on a first portion of the single substrate for detecting temperature; a pressure sensor formed on a second portion of the single substrate for detecting intracranial pressure; and an oxygen sensor formed on a third portion of the single substrate for detecting oxygen concentration. In particular, sensing portions of the temperature sensor, the oxygen sensor and the pressure sensor, respectively, are formed at different layers of the sensor device. There is also provided an integrated multimodal sensor system incorporating the sensor device and the associated methods of fabrication.

18 Claims, 18 Drawing Sheets

(51) Int. Cl.
A61B 5/03 (2006.01)
A61B 5/145 (2006.01)
A61B 5/1486 (2006.01)

(52) U.S. Cl.
CPC .............. *A61B 5/01* (2013.01); *A61B 5/031* (2013.01); *A61B 5/14503* (2013.01); *A61B 5/14542* (2013.01); *A61B 5/14865* (2013.01); *A61B 5/4064* (2013.01); *A61B 2562/028* (2013.01); *A61B 2562/0247* (2013.01); *A61B 2562/0271* (2013.01); *A61B 2562/063* (2013.01); *A61B 2562/125* (2013.01); *A61B 2562/164* (2013.01)

(56) References Cited

U.S. PATENT DOCUMENTS

| | | | | |
|---|---|---|---|---|
| 7,621,878 B2* | 11/2009 | Ericson | ................ | A61B 5/0031 128/903 |
| 8,095,197 B2* | 1/2012 | Santini, Jr. | ........... | A61B 5/1486 600/309 |
| 8,097,926 B2* | 1/2012 | De Graff | .......... | H01L 27/14687 257/419 |
| 8,172,459 B2* | 5/2012 | Abreu | .................. | A61B 5/0002 374/208 |
| 8,536,667 B2* | 9/2013 | de Graff | .......... | H01L 27/14687 257/419 |
| 8,628,493 B2* | 1/2014 | Ahn | .................. | A61M 37/0015 604/27 |
| 9,119,530 B2* | 9/2015 | Abreu | .................. | A61B 5/0002 |
| 9,186,060 B2* | 11/2015 | De Graff | .......... | H01L 27/14687 |
| 9,662,069 B2* | 5/2017 | De Graff | .......... | H01L 27/14687 |
| 2005/0096587 A1* | 5/2005 | Santini, Jr. | ........... | A61B 5/1486 604/66 |
| 2007/0106172 A1* | 5/2007 | Abreu | .................. | A61B 5/0002 600/549 |
| 2008/0269573 A1* | 10/2008 | Najafi | .................. | A61B 5/0031 600/301 |
| 2009/0296780 A1* | 12/2009 | Lee | ......................... | G01K 7/01 374/178 |
| 2009/0297574 A1* | 12/2009 | Ahn | ........................ | A61B 5/031 424/422 |
| 2012/0316459 A1* | 12/2012 | Abreu | .................. | A61B 5/0002 600/549 |
| 2015/0038949 A1* | 2/2015 | Singh | ................ | A61M 39/0247 604/891.1 |
| 2016/0081622 A1* | 3/2016 | Abreu | .................. | A61B 5/0002 600/549 |
| 2017/0020402 A1* | 1/2017 | Rogers | .................. | A61B 5/031 |
| 2017/0095205 A1* | 4/2017 | Abreu | .................. | A61B 5/0002 |

OTHER PUBLICATIONS

A continuous monitoring of cerebral substrate delivery and clearance: initial experience in 24 patients with severe acute brain injuries by Zauner A1, Doppenberg Em, Woodward JJ, Choi SC, Young HF, Bullock R.; Neurosurgery, vol. 41, Issue 5, Nov. 1997, pp. 1082-1093.
International Search Report dated Sep. 5, 2014 for related PCT Application No. PCT/SG2014/000274; 4 pages.
International Preliminary Report on Patentability dated Apr. 29, 2015 for related PCT Application No. PCT/SG2014/000274; 4 pages.
Written Opinion dated Sep. 5, 2014 for related PCT Application No. PCT/SG2014/000274; 4 pages.

* cited by examiner

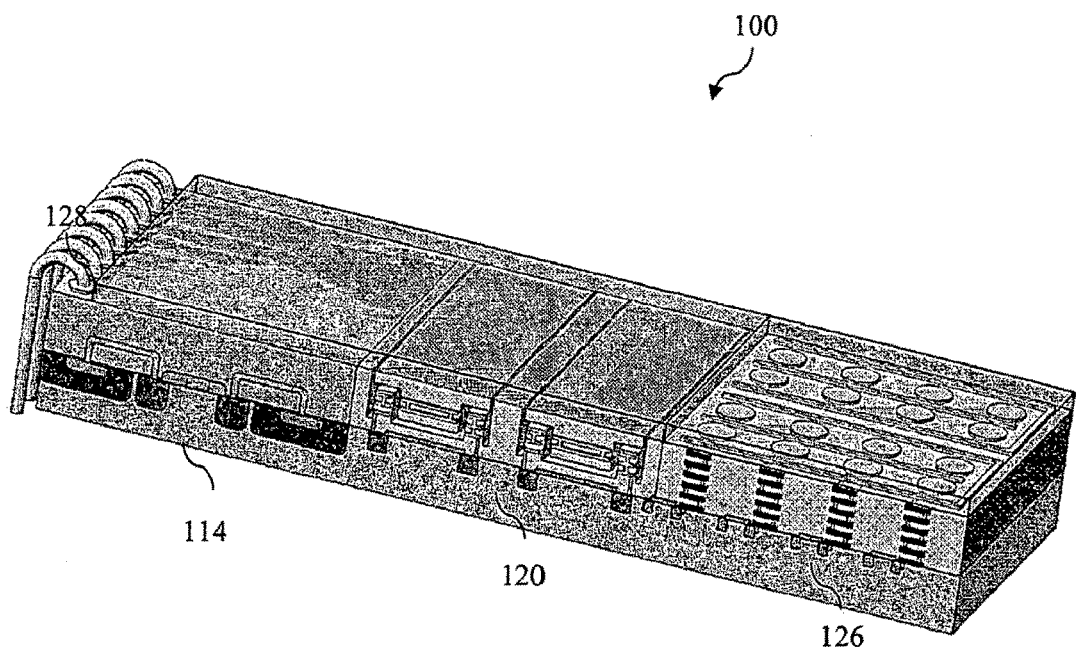
FIG. 11
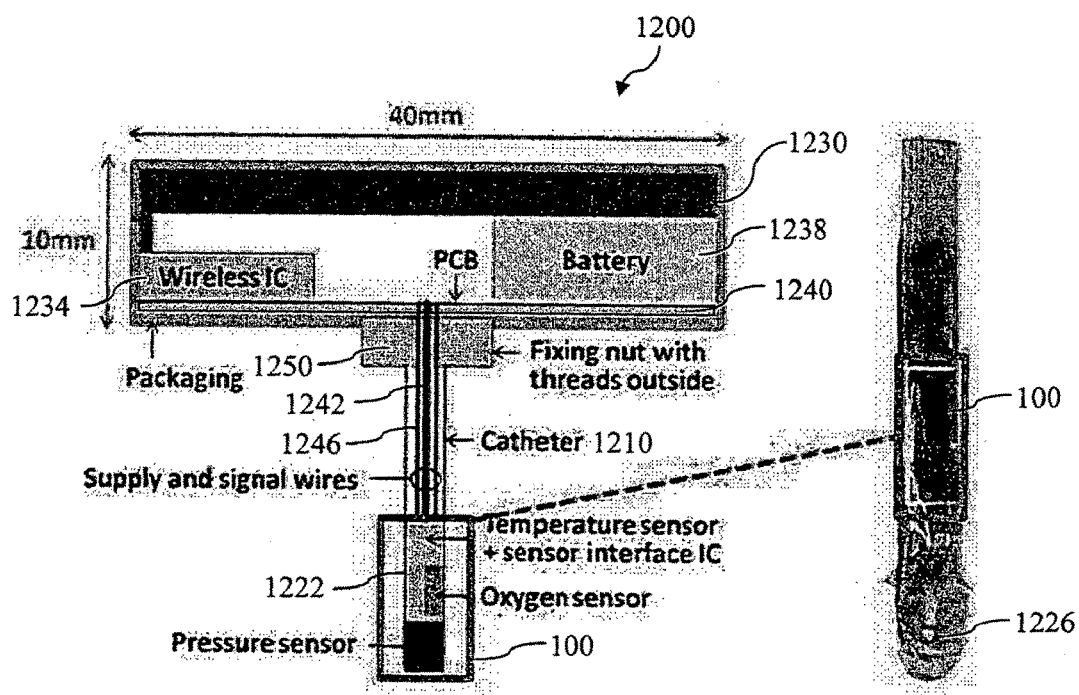
FIG. 12A  FIG. 12B

INTEGRATED MULTIMODAL SENSOR DEVICE FOR INTRACRANIAL NEUROMONITORING

CROSS-REFERENCE TO RELATED APPLICATIONS

This patent application is a U.S. National Phase Application under 35 U.S.C. § 371 of International Application No. PCT/SG2014/000274, filed Jun. 12, 2014, entitled INTEGRATED MULTIMODAL SENSOR DEVICE FOR INTRACRANIAL NEUROMONITORING, which claims priority to Singapore Patent Application No. 201304550-5, filed Jun. 12, 2013.

FIELD OF INVENTION

The present invention generally relates to an integrated multimodal sensor device for intracranial neuromonitoring, a multimodal sensor system for intracranial neuromonitoring comprising the integrated multimodal sensor device, and methods of fabrication thereof.

BACKGROUND

Traumatic brain injury (TBI) is a worldwide phenomenon that has devastating consequences to the patients and the society. The key to TBI management is the capability to control the intracranial pressure (ICP) through accurate monitoring the intracranial pressure, brain oxygenation, and brain temperature in the critical period. Any sudden increase in ICP have to be released either through the drainage of the excess cerebrospinal fluid or by chemotherapy. In a conventional TBI management, standalone pressure sensors, oxygen sensors, and temperature sensors in forms of miniaturized catheters are widely used in intensive care units. An external bolt system is typically used to attach the sensors to the skull to grasp the implanted catheters firmly in the patient's head. Custom data acquisition equipment may then be connected to the catheters directly through the bolt system for signal processing and real-time display of the sensed data from the sensors.

Practically, with the above-described approach, the inserted bolt size (thus the burr hole size) cannot be made small as it has to hold the 3 implanted catheters, and this extra space is more susceptible to bleeding and infection. Furthermore, the individual catheters are configured as a sensing device only, therefore signal conditioning and processing are done entirely by the external equipment.

A need therefore exists to provide a sensor device for intracranial neuromonitoring which seeks to overcome, or at least ameliorate, one or more of the deficiencies of the conventional art mentioned above. It is against this background that the present invention has been developed.

SUMMARY

According to a first aspect of the present invention, there is provided a monolithically integrated multimodal sensor device for intracranial neuromonitoring, the sensor device comprising:
a single substrate;
a temperature sensor formed on a first portion of the single substrate for detecting temperature;
a pressure sensor formed on a second portion of the single substrate for detecting intracranial pressure; and
an oxygen sensor formed on a third portion of the single substrate for detecting oxygen concentration,
wherein sensing portions of the temperature sensor, the oxygen sensor and the pressure sensor, respectively, are formed at different layers of the sensor device.

Preferably, the sensing portion of the temperature sensor is formed at the single substrate, the sensing portion of the pressure sensor is formed at intra-metal layers of the sensor device, and the sensing portion of the oxygen sensor is formed at a top metal layer of the sensor device.

Preferably, the temperature sensor comprises one or more transistors, and the sensing portion of the temperature sensor includes an active region of the respective one or more transistors.

Preferably, the transistor is a parasitic vertical PNP transistor.

Preferably, the pressure sensor comprises one or more capacitive MEMS pressure sensors, and the sensing portion of the pressure sensor includes a movable electrode of the respective one or more capacitive MEMS pressure sensors.

Preferably, the oxygen sensor comprises a switchable array of oxygen sensor elements, and the sensing portion of the oxygen sensor comprises a working electrode of the respective oxygen sensor elements.

Preferably, the oxygen sensor is configured to switch to one of the oxygen sensor elements to provide the oxygen level reading which satisfies a predetermined sensitivity level.

Preferably, the sensor device further comprises one or more application-specific integrated circuits formed on the single substrate for processing readings from the temperature sensor, the oxygen sensor, and the oxygen sensor.

According to a second aspect of the present invention, there is provided a method of fabricating a monolithically integrated multimodal sensor device for intracranial neuromonitoring, the method comprising:
providing a single substrate;
forming a temperature sensor on a first portion of the single substrate for detecting temperature;
forming a pressure sensor on a second portion of the single substrate for detecting intracranial pressure; and
forming an oxygen sensor on a third portion of the single substrate for detecting oxygen concentration,
wherein sensing portions of the temperature sensor, the oxygen sensor and the pressure sensor, respectively, are formed at different layers of the sensor device.

Preferably, the sensing portion of the temperature sensor is formed at the single substrate, the sensing portion of the pressure sensor is formed at intra-metal layers of the sensor device, and the sensing portion of the oxygen sensor is formed at a top metal layer of the sensor device.

Preferably, the temperature sensor comprises one or more transistors, and the sensing portion of the temperature sensor includes an active region of the respective one or more transistors.

Preferably, the transistor is a parasitic vertical PNP transistor.

Preferably, the pressure sensor comprises one or more capacitive MEMS pressure sensors, and the sensing portion of the pressure sensor includes a movable electrode of the respective one or more capacitive MEMS pressure sensors.

Preferably, the oxygen sensor comprises a switchable array of oxygen sensor elements, and the sensing portion of the oxygen sensor comprises a working electrode of the respective oxygen sensor elements.

Preferably, the oxygen sensor is configured to switch to one of the oxygen sensor elements to provide the oxygen level reading which satisfies a predetermined sensitivity level.

Preferably, the method further comprises forming one or more application-specific integrated circuits on the single substrate for processing readings from the temperature sensor, the oxygen sensor, and the oxygen sensor.

According to a third aspect of the present invention, there is provided an integrated multimodal sensor system for intracranial neuromonitoring, the sensor system comprising:

a flexible catheter;

a flexible substrate;

a monolithically integrated multimodal sensor device according to the above-described first aspect of the present invention disposed on the flexible substrate and within a sensing end portion of the flexible catheter; and a guide tip member extending from the sensing end portion of the flexible catheter to facilitate penetration and directional guidance of the flexible catheter during insertion of the sensing end portion of the flexible catheter into the cranium.

Preferably, the guide tip member has a rounded tip and is made of silicone.

Preferably, the sensor system further comprises a housing including therein a wireless communication module for receiving sensed data from the sensor device and an antenna for transmitting the sensed data wirelessly to one or more remote extracranial devices.

According to a fourth aspect of the present invention, there is provided a method of forming an integrated multimodal sensor system for intracranial neuromonitoring, the method comprising:

providing a flexible catheter;

providing a flexible substrate;

disposing a monolithically integrated multimodal sensor device according to the above-described first aspect of the present invention on the flexible substrate and within a sensing end portion of the flexible catheter; and forming a guide tip member extending from the sensing end portion of the flexible catheter to facilitate penetration and directional guidance of the flexible catheter during insertion of the sensing end portion of the flexible catheter into the cranium.

BRIEF DESCRIPTION OF THE DRAWINGS

Embodiments of the present invention will be better understood and readily apparent to one of ordinary skill in the art from the following written description, by way of example only, and in conjunction with the drawings, in which:

FIG. 11 an example completed sensor device (or sensor chip) fabricated according to an example embodiment of the present invention;

FIGS. 12A to 12C depict the sensor device packaged for in-vivo application (an integrated multimodal sensor system) according to an example embodiment of the present invention;

DETAILED DESCRIPTION

Intracranial neuromonitoring of various physiologic parameters is critical in neurological disorders such as traumatic brain injury (TBI), hydrocephalus and tumours that can cause changes in the pressure within the skull of a subject. Example embodiments of the present invention provide a monolithically integrated multimodal sensor device for intracranial neuromonitoring, including a temperature sensor for detecting intracranial temperature, a pressure sensor for detecting intracranial pressure, and an oxygen sensor for detecting oxygen concentration. In particular, in the example embodiments, the temperature sensor, the pressure sensor, and the oxygen sensor are integrated on a single substrate. This advantageously enables the sensor device having intracranial temperature, intracranial pressure and oxygen concentration sensing capabilities to be provided with a single catheter, thus eliminating the need to provide multiple catheters for obtaining multiple physiologic parameters. As a result, the size of the bolt or burr hole required to perform intracranial neuromonitoring can be minimised, thus making it less susceptible to bleeding and infection. The overall intracranial neuromonitoring process is also greatly simplified since, for example, less catheters are involved.

Figure 1A:
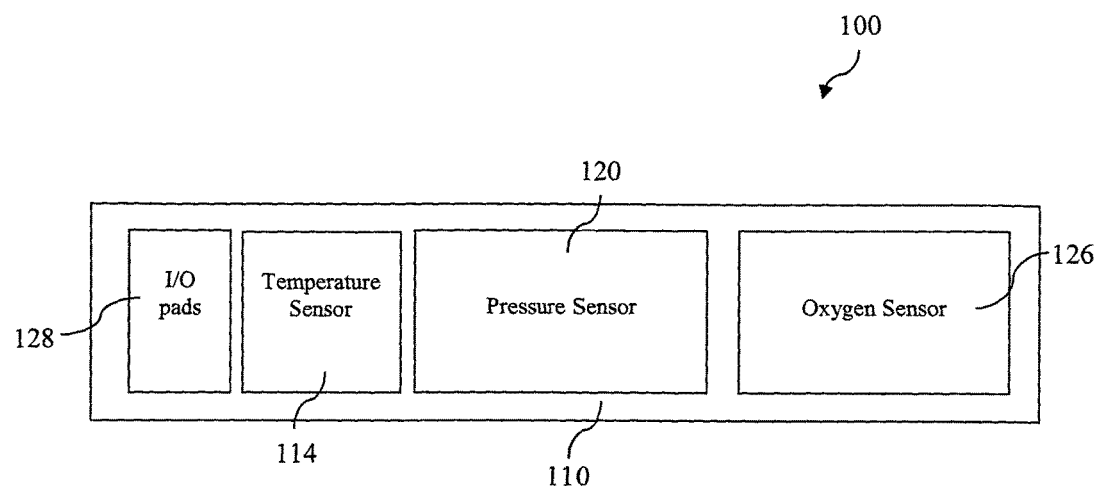
FIG. 1A depicts a schematic top view of an example monolithically integrated multimodal sensor device for intracranial neuromonitoring according to an example embodiment of the present invention.
Figure 1B:
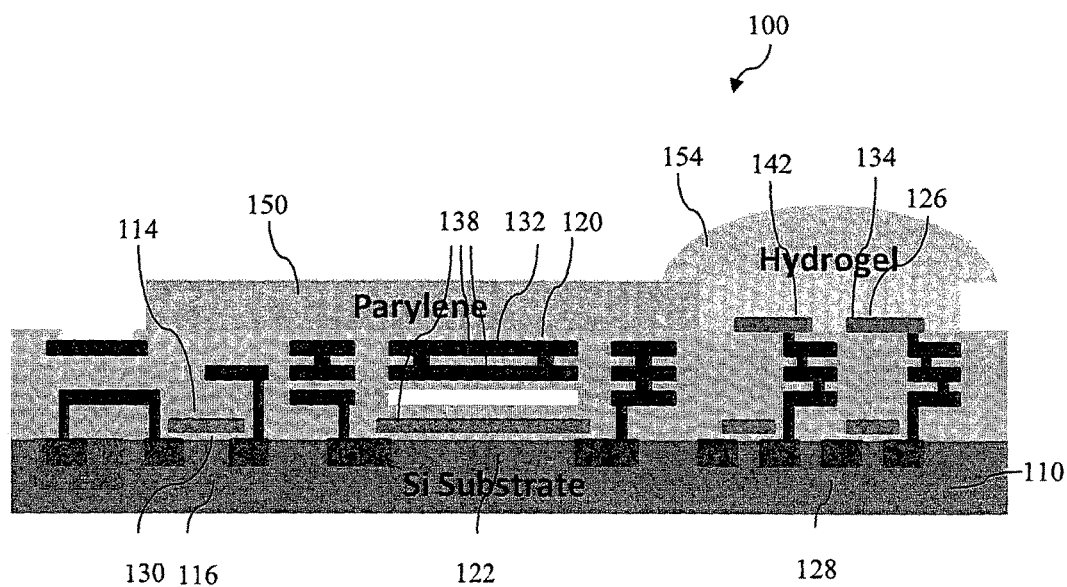
FIG. 1B depicts a schematic cross-sectional view of the example sensor device shown in FIG. 1A.

FIG. 1A depicts a schematic top view of an example monolithically integrated multimodal sensor device 100 for intracranial neuromonitoring according to an example embodiment of the present invention. FIG. 1B depicts a schematic cross-sectional view of the example sensor device 100. As shown, the sensor device 100 comprises a single substrate (preferably, silicon substrate) 110, a temperature sensor 114 formed on a first portion 116 of the single substrate 110 for detecting intracranial temperature, a pressure sensor 120 formed on a second portion 122 of the single substrate 110 for detecting intracranial pressure, and an oxygen sensor 126 formed on a third portion 128 of the single substrate 110 for detecting oxygen concentration. In particular, sensing portions 130, 132, 134 of the temperature sensor 114, the pressure sensor 120 and the oxygen sensor 126, respectively, are formed at different layers of the sensor device 100.

In the example embodiment as shown in FIG. 1B, the sensing portion 130 of the temperature sensor 114 is formed at the single substrate 110, the sensing portion 132 of the pressure sensor 120 is formed at intra-metal layers 138 of the sensor device 100, and the sensing portion 134 of the oxygen sensor 126 is formed at a top metal layer 142 of the sensor device 100. In this regard, forming the sensing portions 130, 132, 134 of the three sensors 114, 120, 126 at different layers of the sensor device 100 enables the three sensors 114, 120, 126 to be formed integrally on a single substrate 110 (i.e., integrated into a single chip) using a customized integrated fabrication flow. The steps in fabricating the integrated multimodal sensor device 100 will be described in detail later below with reference to FIGS. 10A to 10Z.

Figures 2, 3A:
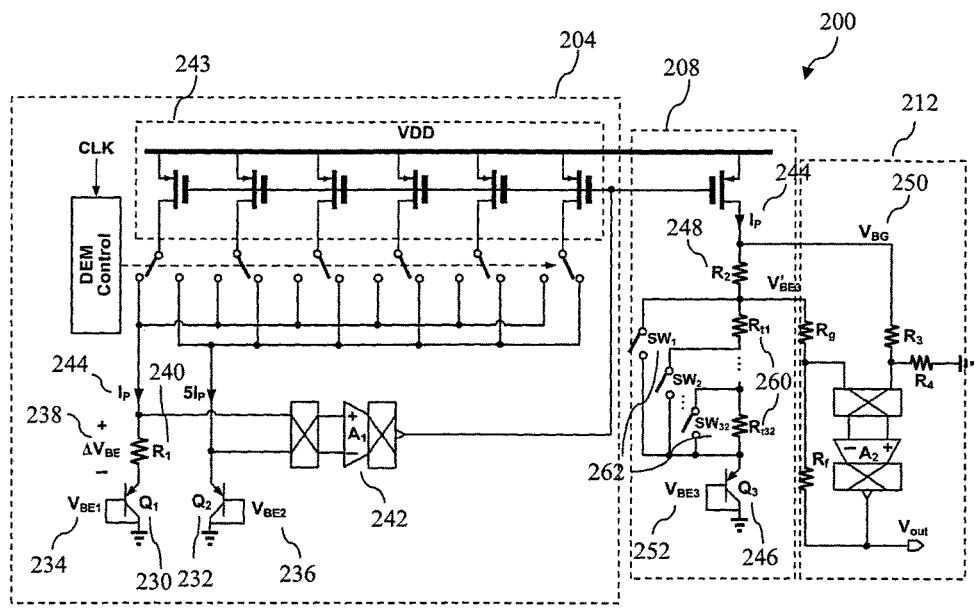
FIG. 2 depicts a schematic diagram of an example temperature sensor circuit according to an embodiment of the present invention.
FIG. 3A depicts a cross-sectional view of one example capacitive MEMS pressure sensor according to an embodiment of the present invention.

In an example embodiment, the temperature sensor 114 is realised by one or more transistors, preferably, parasitic vertical PNP transistors. As an example, FIG. 2 shows a schematic diagram of an example temperature sensor circuit 200 which includes a PTAT (Proportional To Absolute Temperature) current generator 204, a bandgap reference 208 and a $V_{BE}$ amplifier 212. In the PTAT current generator 204, two identical PNP transistors $Q_1$ 230 and $Q_2$ 232 are biased in a current ratio of 1 to 5. The difference of the base emitter voltage $V_{BE1}$ 234 and $V_{BE2}$ 236 is a PTAT voltage $\Delta V_{BE}$ 238 which can be sensed by resistor $R_1$ 240 and feedback to the chopper stabilized error amplifier $A_1$ 242. The current ratio of 1 to 5 is implemented by randomly scrambling the PMOS current sink 243 through dynamic element matching (DEM). As a result, the impact of the device mismatch to the circuit operation point is minimized, and the current flowing through the resistor $R_1$ 240 is a PTAT current $I_P$ 244. This PTAT current source 244 is mirrored to bias a NPN transistor $Q_3$ 246 having an identical size as transistors $Q_1$ 230 and $Q_2$ 232, and produces a PTAT voltage drop across the resistor $R_2$ 248. The bandgap voltage $V_{BG}$ 250 is obtained by summing the base-emitter voltage $V_{BE3}$ 252 and the PTAT voltage across $R_2$ 248. The process spread of the saturation current, the finite value of the forward current gain, and the base resistance of transistor $Q_3$ 246 all contribute to base emitter voltage $V_{BE3}$ 252 mismatch. In a preferred embodiment, a one-point calibration is implemented to compensate the $V_{BE3}$ 252 mismatch. A 5-bit on-chip resistor trimming network including resistors ($R_{t1-t32}$) 260 and switches ($SK_{t1-t32}$) 262 is used to provide coarse $V_{BE3}$ calibration with 32 steps of PTAT voltage tuning at room temperature.

In the example embodiment, the sensing portion 130 of the temperature sensor 114 includes an active region of the respective one or more transistors. Preferably, the transistors are fabricated in the silicon substrate 110 by CMOS foundries and the operation of a PNP transistor can be expressed by the following Equation:

$$I_c = I_s \exp\left(\frac{V_{BE}}{V_T}\right) \quad (1)$$

where $I_s$ is the saturation current, $V_{BE}$ is the base emitter voltage, $V_T$ is the thermal voltage, and $I_c$ is the collector current of the bipolar transistor. As can be seen from Equation 1, the saturation current ($I_s$) has a strong temperature dependency, and the temperature sensor 114 has been found to exhibit a temperature sensitivity of about −2 mV/° C. with respect to $V_{BE}$.

However, fabrication mismatch may exists in standard CMOS process, and it has been found that the model as shown in Equation 1 is only good as long as the process parameters such as the saturation current ($I_s$) are well controlled. But the limited current gain associated with the PNP transistor, the finite value of the base resistance, the high level injection, and the Early effect all affect the accuracy and the sensitivity of the temperature sensor 114. Therefore, in a preferred embodiment, $V_{BE}$ calibration is implemented to improve the accuracy of the temperature sensor 114 as for example described above with reference to FIG. 2 where resistor trimming is the chosen technique to achieve the $V_{BE}$ calibration. Various trimming circuit implementations have been disclosed in the art to address temperature sensor mismatches and yield good accuracies. Therefore, the present invention is not limited to the trimming circuit as shown in FIG. 2 and a person skilled in the art would be able to apply any other appropriate trimming circuit known in the art to the temperature sensor 114 to improve sensing accuracy. The steps in fabricating the temperature sensor 114 will be described in detail later below as part of the process of fabricating the integrated multimodal sensor device 100.

In an example embodiment, the pressure sensor 120 is realised by one or more capacitive MEMS pressure sensors in CMOS. A cross-sectional view of one example capacitive MEMS pressure sensor 300 is schematically illustrated in FIG. 3A. The pressure sensor 300 is advantageously simple as it involves a front side release only. In the example embodiment, the MEMS configuration utilizes two metals layers 314, 315 (M4 and M5) and three intra-metal dielectric layers 310, 311, 312 (IMD3, IMD4, and IMD5) (e.g., $SiO_2$) for the movable electrode 318, and one metal layer 326 (M2) and two intra-metal dielectric layers 327 (IMD2 and IMD1) for the stationary electrode 322 under the movable electrode 318. In order to create room for the movable electrode 318, a first via 330, a second via 334 and a third via 338 have to be etched away first and subsequently the intra-metal layer under the movable electrode 318 (i.e., M3 to form a cavity 350). In this example, the sensing portion 132 of the pressure sensor 120 includes the movable electrode 318 of the respective one or more capacitive MEMS pressure sensors. For example, the etchant involved is a mixture of $H_2SO_4$+ $H_2O_2$ (2:1) heated at 100° C. over 120 minutes. The steps in fabricating the pressure sensor 300 will be described in detail later below as part of the process of fabricating the integrated multimodal sensor device 100.

Figure 3B:
FIGS. 3B and 3C depict the top view and the cross-sectional view of the released membrane of the pressure sensor captured in the scanning electro-microphotograph (SEM), respectively.
Figure 3C:
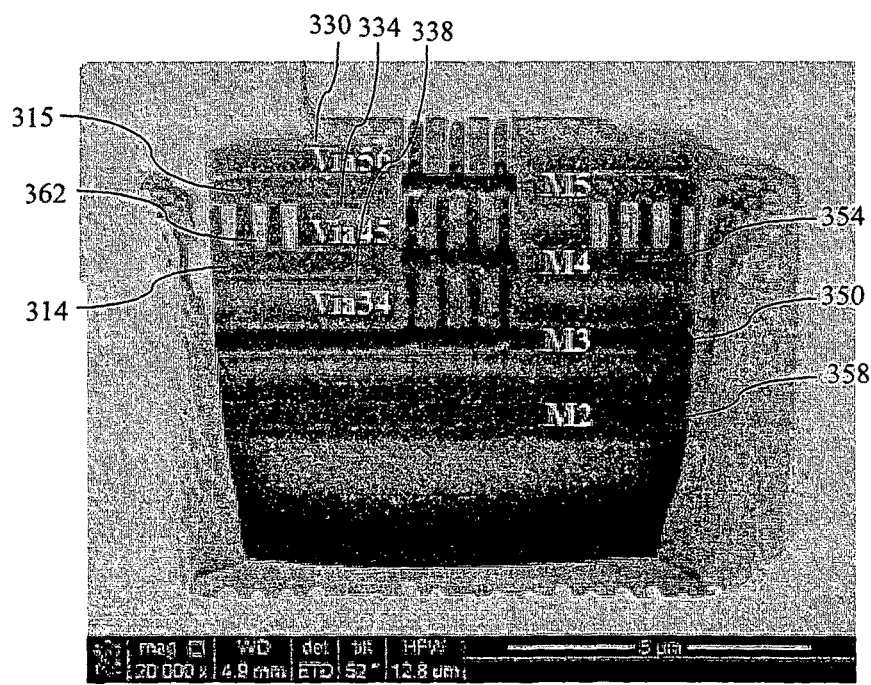

The top view and the cross-sectional view of the released membrane are captured in the scanning electro-microphotograph (SEM) and illustrated in FIGS. 3B and 3C, respectively. In FIG. 3C, the existence of the cavity 350 can be observed (which is shown in a dark shading) between the top plate 354 and the bottom plate 358. It can also be observed that the non-etched via 362 (which is shown in a light shading) connecting metal layer M4 314 and metal layer M5 315 within the top plate 354. The movable electrode 318 is formed using metal layers M4 314 and M5 315 and the vias 45 334 have two functions depending on the layout location. A first function is to serve as a path to release the structure (that is, to etch away the materials that metals layers and vias are made of, for example, Aluminium (Al) and Tungsten (W), respectively) and a second function is to connect M4 314 and M5 314 layers. As a final step, a protective polymer coating material 150 (preferably, Parylene-C) is patterned to encapsulate the pressure sensor's active area 132 using standard lithograph. In an example implementation, the MEMS pressure sensor 120 is configured as an array of 9 capacitors with a trimming circuit to achieve good accuracy and sensitivity. Various trimming circuit implementations have been disclosed to address pressure sensor mismatches and yield good accuracies. A person skilled in the art would be able to apply an appropriate trimming circuit known in the art to the pressure sensor 120 to improve sensing accuracy and thus it is not necessary to be described herein.

Figure 4:
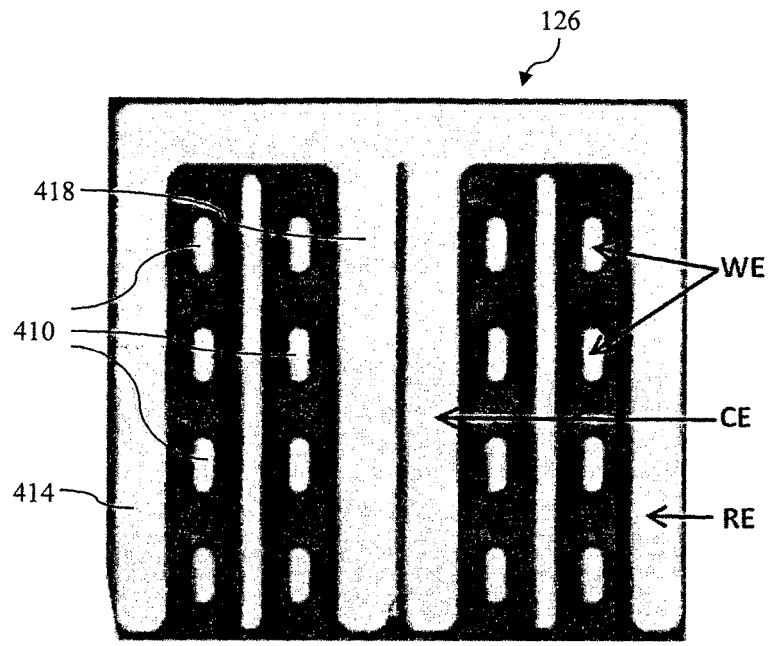
FIG. 4 depicts an exemplary the oxygen sensor configured as a 3-electrode system according to an embodiment of the present invention.

In an embodiment, the oxygen sensor 126 comprises a switchable array of oxygen sensor elements 410. A top view of oxygen sensor 126 in CMOS made up of an array of 16 oxygen sensor elements 410 is illustrated in FIG. 4. Preferably, the oxygen sensor elements 410 are clark-type dissolved oxygen sensors. FIG. 4 illustrates the oxygen sensor 126 configured as a 3-electrode system (i.e., working electrode 410, counter electrode 414, and reference electrode 418). It will be appreciated that the oxygen sensor 126 of the present invention is not limited to a 3-electrode system. For example, the oxygen sensor 126 may be configured as a 2-electrode system (i.e., working electrode and reference electrode). In this embodiment, the sensing portion 134 of the oxygen sensor 126 comprises the oxygen sensor elements (working electrode) 410.

In an example embodiment, to fabricate the working electrode 410 on the top metal layer 142 of the sensor device 100, platinum is used as the raw material to form the working electrode 410. The working electrode 410 can be attached to the CMOS top metal layer 142 (e.g., aluminium) through a layer of 20 nm thick titanium in between the platinum working electrode 410 and the top metal layer 142. The actual physical shape of the working electrode 410 as shown in FIG. 4 can be patterned by E-beam evaporator together with lift-off. To maximize the working electrode 410 sensitivity, the following Equation can be used to relate the sensitivity with the area of working electrode 410:

$$i = \frac{nA_s FDC_{DO}}{\delta} \quad (2)$$

where n is the number of exchanged electrons, $A_s$ is the area of the working electrode 410, F is Faraday's constant, D is the diffusivity, $C_{DO}$ is the dissolved oxygen concentration in a given sample, $\delta$ is the thickness of the selective permeable membrane, and i is the reduction current. By way of example only, the unit size of 25 μm×50 μm working electrode 410, approximately 250 pA reduction current can be generated for every mmHg dissolved oxygen at room temperature.

In an embodiment, specific polymers 154, whose physical structures are selective permeable, are used to encapsulate the oxygen sensor 126. For instance, a nickel-salen polymer can be used as a solid electrolyte, and this polymer was found to be able to increase the sensitivity of the platinum working electrode 410. On the other hand, NAFION which is commercially available can be chosen as a solid electrolyte. NAFION has been used as a solid electrolyte which permits oxygen transport across its structure. Unfortunately, NAFION deposition on the platinum electrode 410 cannot be done using similar CMOS processing. Instead, it is usually deposited in drop-cast which is subjected to coating thickness mismatch.

All the sensors 114, 120, 126 fabricated in the sensor device 100 are calibrated to achieve a certain degree of accuracy. For instance, the specifications of both the pressure sensor 120 and the oxygen sensor 126 are configured to achieve an inaccuracy of ±1 mmHg whereas the temperature sensor 114 is ±0.2° C. for the typical sensing range. Due to the post-processing mismatch, the fabricated sensors suffer a certain degree of mismatch relative to its operating parameters. In the capacitive MEMS pressure sensor 120 or the PNP-based temperature sensor 114, sensor mismatches are relatively well modelled. As mentioned hereinbefore, various trimming circuit implementations have been disclosed to address pressure sensor and temperature sensor mismatches and yield good accuracies. Therefore, a person skilled in the art would be able to apply appropriate trimming circuits known in the art to the temperature sensor 114 and the pressure sensor 120 to improve sensing accuracy.

But on the other hand, the challenge in calibrating the electrochemical oxygen sensor 126 comes from the non-standard fabrication of the oxygen sensor 126. Specifically, the non-standard fabrication in developing the oxygen sensor 126 is the hydrogel 154 deposition, for example, the deposition of NAFION by drop-cast as mentioned above. The coating thickness of this hydrogel 154 is highly subjected to mismatch which is a significant factor resulting in the inaccuracy of the oxygen sensors 126. In the example embodiment, the oxygen sensor 126 is configured with sensor calibration. In particular, the oxygen sensor 126 comprises a switchable array of oxygen sensor elements 410 is provided to address the above problem. For example, the oxygen sensor 126 comprises 16 switchable working electrodes 410 sharing a common electrode 418 and a reference electrode 414 as illustrated in FIG. 4. In particular, the oxygen sensor 126 is configured to switch to one of the oxygen sensor elements 410 to provide the oxygen level reading which satisfies a predetermined sensitivity level. The specific working electrode element 410 can be activated by evaluating its sensitivity during the sensor calibration procedure. Therefore, the sensitivity of working electrode 410 can be recorded and evaluated against the target sensitivity. If there are more than a single working electrode 410 which can achieve the target sensitivity, the array implementation adds a back up to the system such that any specific sensor failure can be replaced by an available working electrode element 410.

Figure 5:
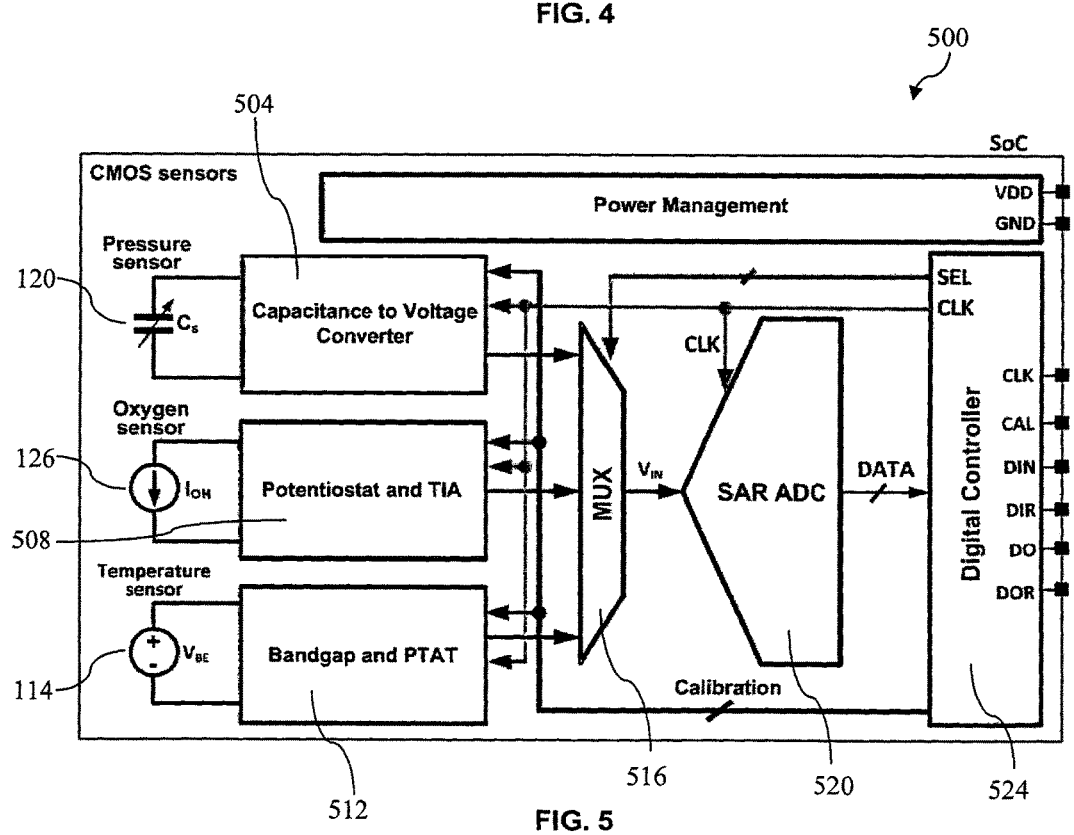
FIG. 5 depicts a schematic diagram of an exemplary ASIC integrally formed on the substrate according to an embodiment of the present invention.

In an embodiment, the sensor device 100 further comprises one or more application-specific integrated circuits (ASIC) integrally formed on the single substrate 110 for processing readings from the temperature sensor, the pressure sensor, and the oxygen sensor. FIG. 5 depicts a schematic diagram of an exemplary ASIC 500 integrally formed on the single substrate 110. The ASIC 500 comprises a pressure sensor interface circuit 504 including a capacitance-to-voltage converter (CVC) for processing readings from the pressure sensor 120, an oxygen sensor interface circuit 508 including a potentiostat and a transimpedance amplifier (TIA) for processing readings from the oxygen sensor 126, and a temperature sensor interface circuit 512 including a bandgap reference and a proportional-to-absolute-temperature (PTAT) voltage generator for processing readings from the temperature sensor 114. In the example embodiment, since the pressure, oxygen and temperature signals have low-frequency variation, the outputs of the sensor interface circuits 504, 508, 512 can be multiplexed to share a single 10-bit SAR ADC (successive approximation analog-to-digital converter) 520 for signal digitization. A digital controller 524 is provided for converting the ADC 520 output to a serial bit stream for communicating with the external devices such as an external data logger.

Figure 6A:
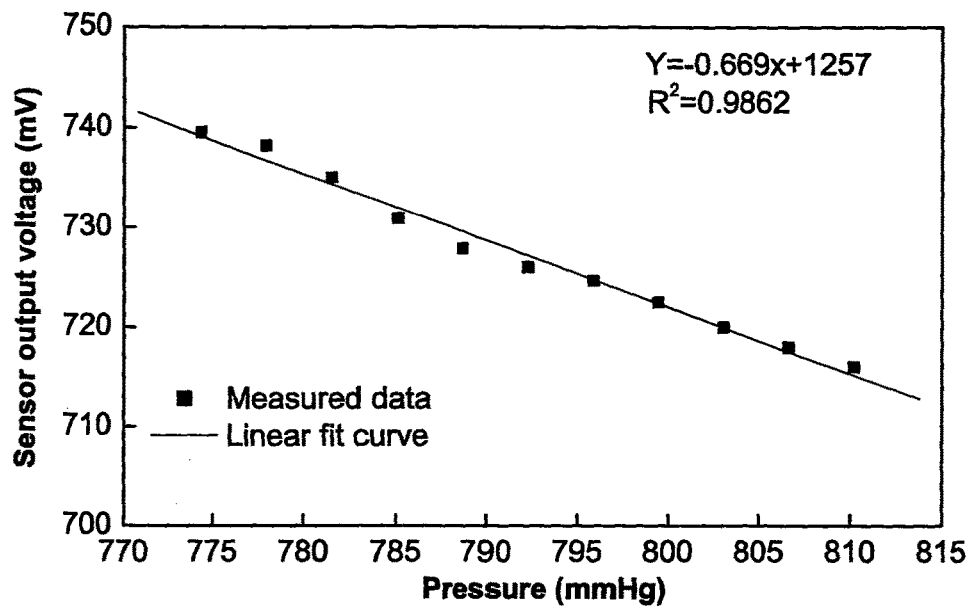
FIG. 6A depicts a graph showing the output response of the pressure sensor versus the pressure applied in an experiment.
Figure 6B:
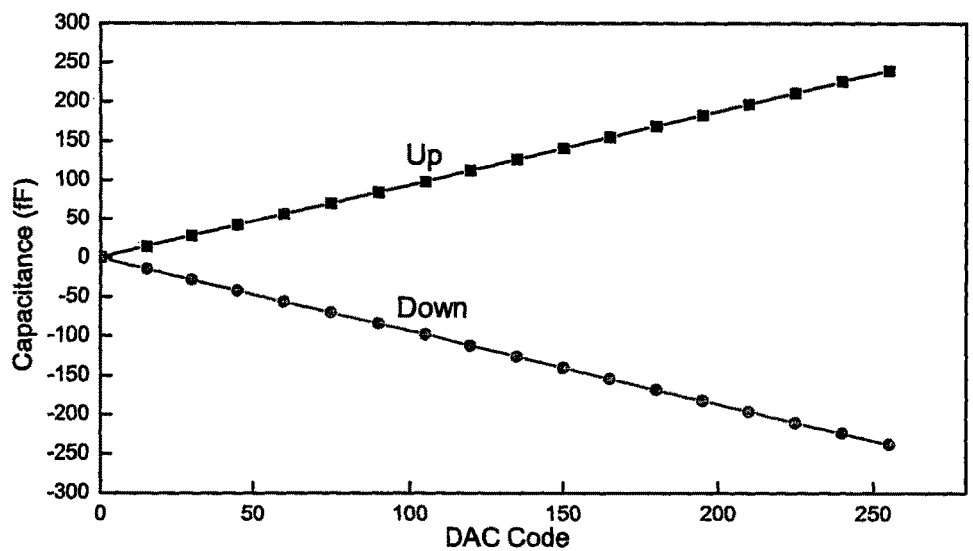
FIG. 6B depicts a graph showing the measured result of pressure sensor capacitance mismatch calibration.

In an experiment, the capacitive MEMS pressure sensor 120 is configured as a capacitance to voltage converter (CVC) for direct signal processing, and FIG. 6A shows the output response of the CVC versus the pressure applied. The linear fit curve has a coefficient of determination ($R^2$) of 0.9862, indicating good linear response of the sensor circuit and the measured sensitivity is 0.67 mV/mmHg. A 14-bit ADC is able to convert this sensitivity into the required resolution. FIG. 6B shows the measured result of pressure sensor capacitance mismatch calibration. It is demonstrated that by changing the resistive DAC trimming code with UP/DOWN control, the trimming circuit can cover a linear tuning range from −237.8 fF to +239.9 fF with 0.93-fF resolution.

Figure 7A:
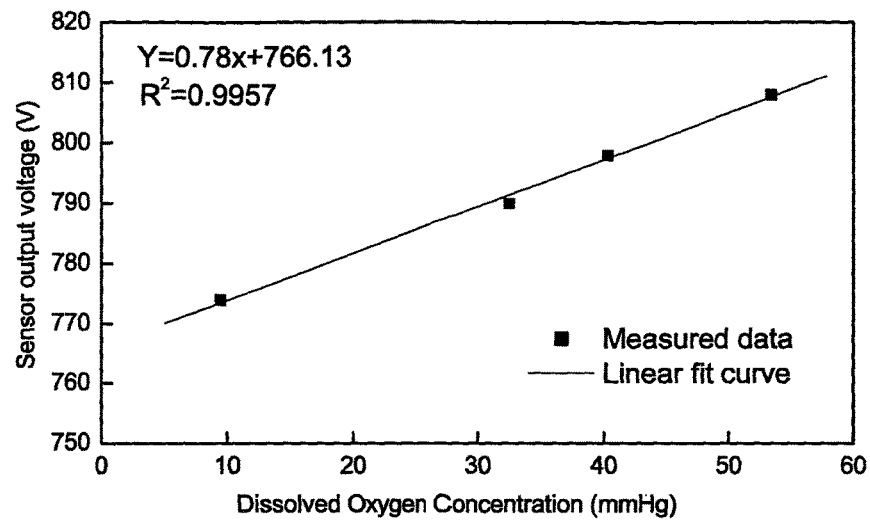
FIG. 7A depicts a graph showing the output response of the oxygen sensor versus dissolved oxygen concentration in an experiment.
Figure 7B:
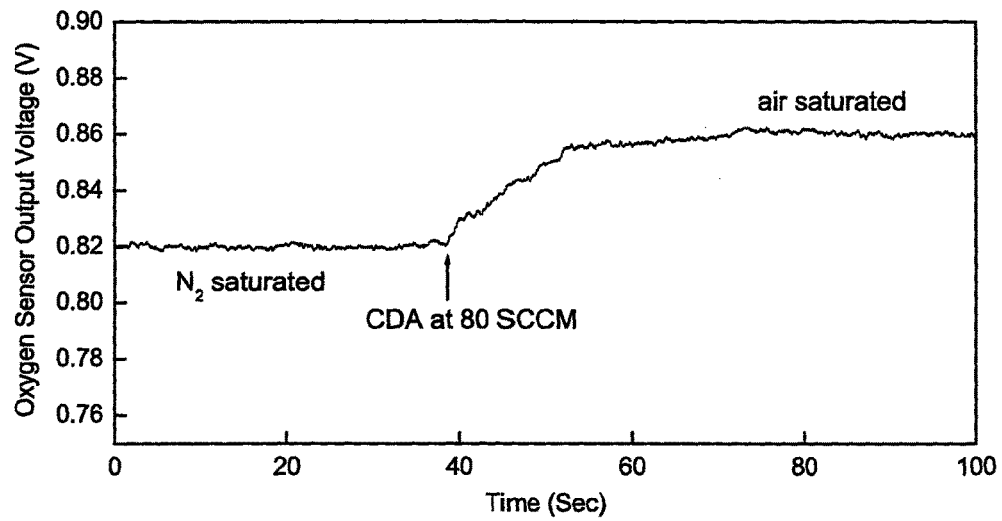
FIG. 7B depicts a graph showing the measured transient response of the oxygen sensor in an aqueous solution from nitrogen-saturated condition to air-saturated condition.

In an experiment, the oxygen sensor 126 is configured as a potentiometer, which outputs a current directly proportional to the concentration of oxygen. The current generated is then further converted to a voltage by a transimpedance amplifier. FIG. 7A is a plot of the output response of the oxygen sensor versus dissolved oxygen concentration and summarizes the measured result of the oxygen sensor 126 performance. Over the measured partial pressure of dissolved oxygen from 10 to 55 mmHg, the linear fit curve has a $R^2$ of 0.9957 and the measured sensitivity is 0.78 mV/mmHg, which is equivalent to an input sensitivity of 194 pA/mmHg. FIG. 7B shows the measured transient response of the oxygen sensor 126 in an aqueous solution from nitrogen-saturated condition to air-saturated condition. FIG. 7B demonstrates the fast response of the oxygen sensor to the change of dissolved oxygen concentration. Again, a 14-bit ADC is able to convert this detected partial pressure of the dissolved oxygen in 1 mmHg resolution.

Figure 8A:
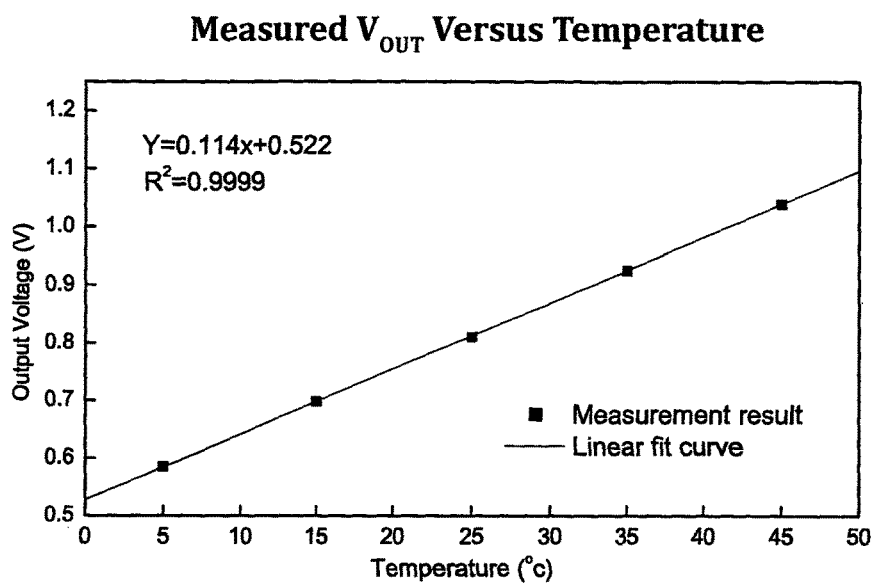
FIG. 8A depicts a graph illustrating the linear output response of the temperature sensor in an experiment.
Figure 8B:
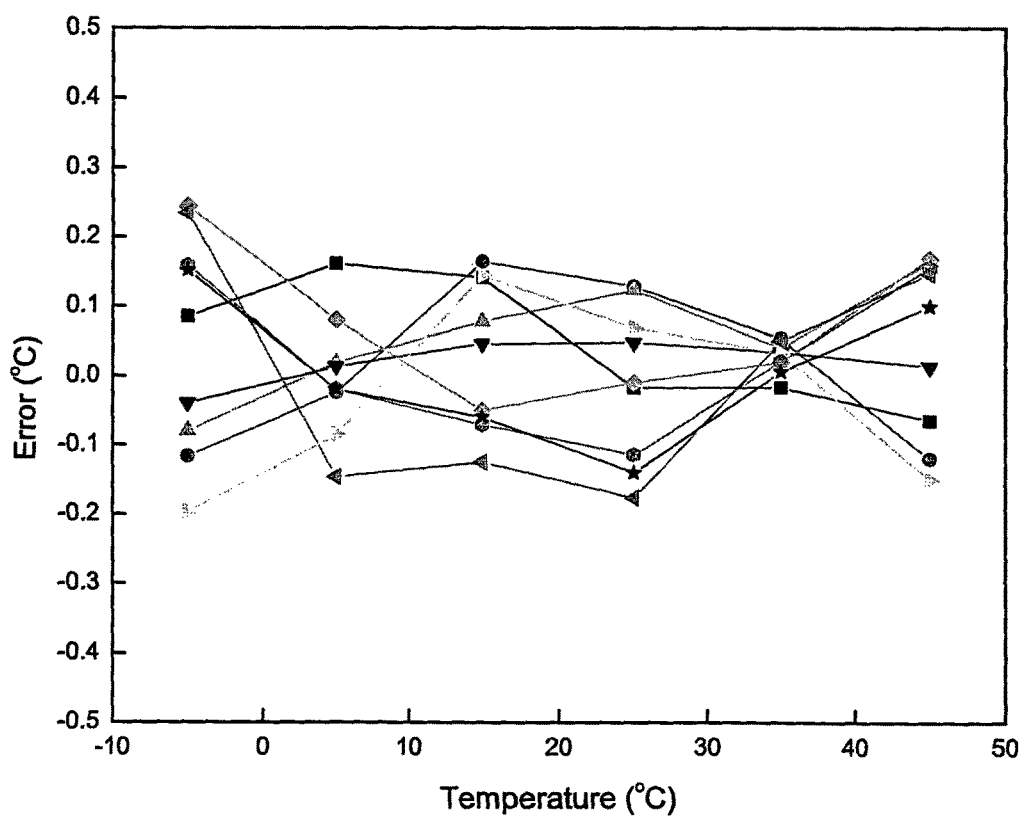
FIG. 8B depicts a graph illustrating the temperature inaccuracy of multiple temperature sensors over the temperature range from −5° C. to 45° C. in an experiment.

In an experiment, the temperature sensor 114 is incorporated in the classical bandgap topology where the output of interest is the base emitter voltage. As the typical sensitivity of the base emitter voltage is about −2 mV/° C., the base emitter voltage is actually connected to a second stage with a gain of 5 to increase the the sensitivity to above 10 mV/° C. In this temperature sensor characterization, 9 chips were evaluated. Since the temperature sensitivity is increased by design, the resolution requirement of the ADC can be reduced from 14 bits to 10 bits. As shown in FIG. 8A, the temperature sensor 114 has a linear output response with $R^2$ of 0.9999, the measured output sensitivity is about 11 mV/° C. when the measurement results of 9 chips are averaged. FIG. 8B illustrates that a temperature inaccuracy of ±0.3° C. is achieved over the temperature range from −5° C. to 45° C. In addition, FIG. 8B shows that after one-point calibration at 35° C., the inaccuracy of the sensors is bound within ±0.2° C. over the target temperature range of 30° C. to 45° C.

Figure 9:
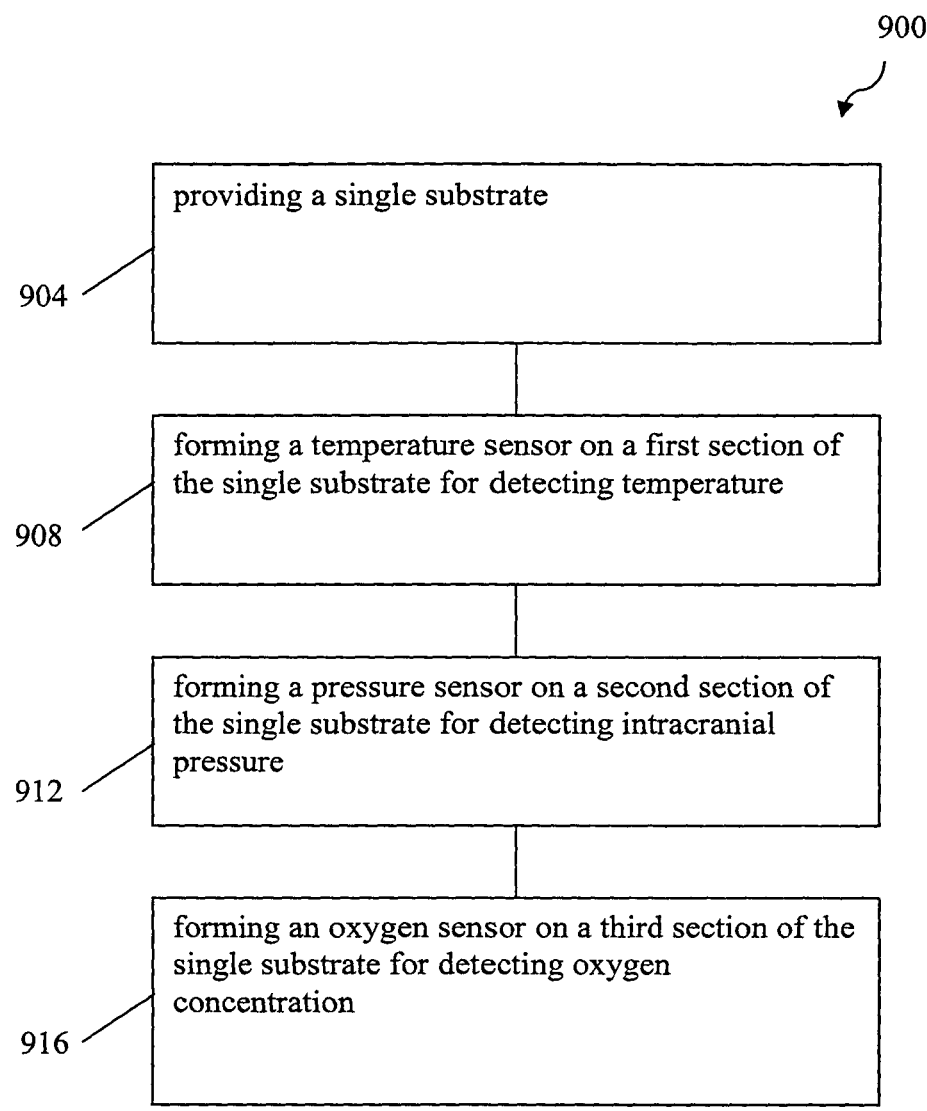
FIG. 9 depicts an overview of a method of fabricating the monolithically integrated multimodal sensor device for intracranial neuromonitoring according to an embodiment of the present invention.

An overview of a method 900 of fabricating the monolithically integrated multimodal sensor device 100 for intracranial neuromonitoring will now be described according to an embodiment of the present invention with reference to FIG. 9. The method 900 comprises a step 904 of providing a single substrate 110 (such as a CMOS substrate), a step 908 of forming a temperature sensor 114 on a first portion 116 of the single substrate 110 for detecting temperature, a step 912 of forming a pressure sensor 120 on a second portion 122 of the single substrate 110 for detecting intracranial pressure, and a step 916 of forming an oxygen sensor 126 on a third portion 128 of the single substrate 110 for detecting oxygen concentration. In a preferred embodiment, steps 908, 912 and 916 are parallel processes (CMOS processes), followed by post-processing steps such as to release the pressure sensor 120 and to deposit the platinum working electrode 410 over the top metal layer 142 of the oxygen sensor 126. In particular, sensing portions 130, 132, 134 of the temperature sensor 114, the pressure sensor 120 and the oxygen sensor 126, respectively, are formed at different layers of the sensor device 100. In an embodiment, the sensing portion 130 of the temperature sensor 114 is formed at the single substrate 110, the sensing portion 132 of the pressure sensor 120 is formed at intra-metal layers 138 of the sensor device 100, and the sensing portion 134 of the oxygen sensor 126 is formed at a top metal layer 142 of the sensor device. In this regard, forming the sensing portions 130, 132, 134 of the three sensors 114, 120, 126 at different layers of the sensor device 100 enables the three sensors 114, 120, 126 to be formed integrally on a single substrate 110 (i.e., integrated into a single chip) using a customized integrated fabrication flow. The steps in fabricating the integrated multimodal sensor device 100 will now be described in further detail according to an example embodiment of the present invention.

Figure 10A:
FIGS. 10A to 10Z shows the steps in fabricating the integrated multimodal sensor device according to an example embodiment of the present invention.
Figure 10B:
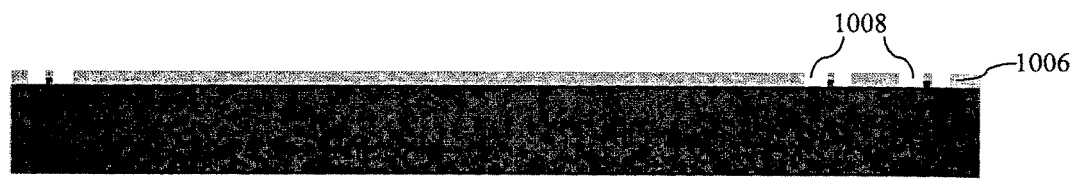
Figure 10C:
Figure 10D:
Figure 10E:
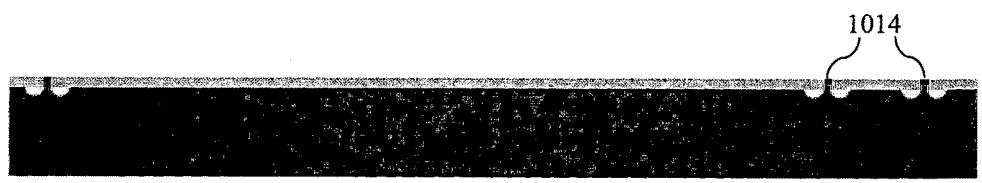
Figure 10F:
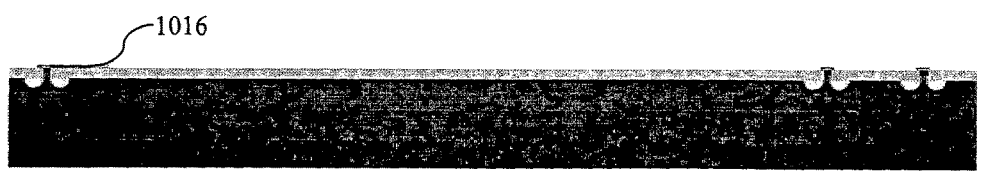

In the example embodiment, the integrated multimodal sensor device 100 is manufactured based on CMOS fabrication process using a 0.18 µm technology of GLOBALFOUNDRIES INC. As a first step, a single piece of blank wafer/substrate (preferably, silicon substrate) 110 is provided as illustrated in FIG. 10A on which the temperature sensor 114, the pressure sensor 120, the oxygen sensor 126 and the associated ASIC 500 are to be formed. A thin layer of gate oxide is deposited to form the NMOS transistors for the temperature sensor 114, oxygen sensor 126 and the ASIC 500, and a polysilicon layer 1004 is formed and patterned as shown in FIG. 10A. Subsequently, as shown in FIG. 10B, an oxide layer 1006 is deposited on the substrate 110 and then patterned at portions 1008 where n+ dopants should be diffused or implanted. FIG. 10B. Then, as shown in FIG. 10C, the n+ regions 1010 of the transistors are formed in the substrate 110 and the oxide layer 1006 is removed. Subsequently, the ILD (interlayer dielectric) 1012 is deposited on the substrate 110 and patterned as shown in FIG. 10D, and the VIA1 1014 is deposited and subjected to CMP (chemical mechanical planarization) as shown in FIG. 10E. The METAL1 (M1) layer 1016 is then deposited on the ILD layer 1012 and patterned as shown in FIG. 10F.

Figure 10G:
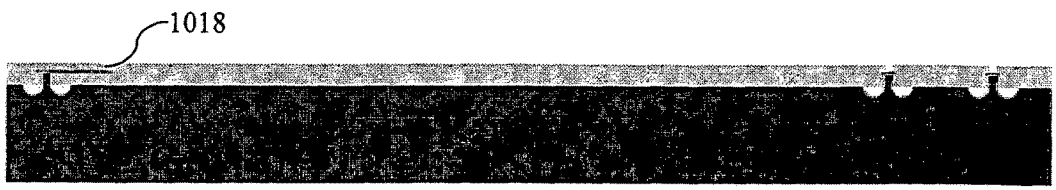
Figure 10H:
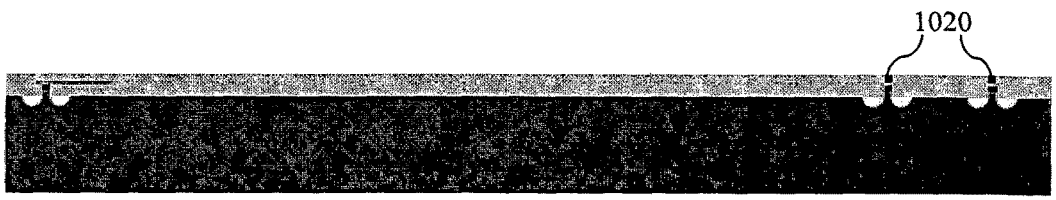
Figure 10I:
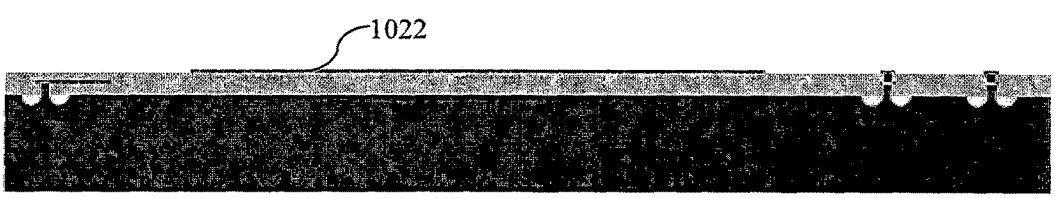

Subsequently, the IMD1 (intra-metal dielectric) layer 1018 is deposited over the METAL1 layer 1016 and ILD layer 1012 and patterned as shown in FIG. 10G, and the VIA12 1020 is deposited and subjected to CMP as shown in FIG. 10H. Then, the METAL2 layer 1022 is deposited over the IMD1 layer 1018 and patterned as shown in FIG. 10I.

Figure 10J:
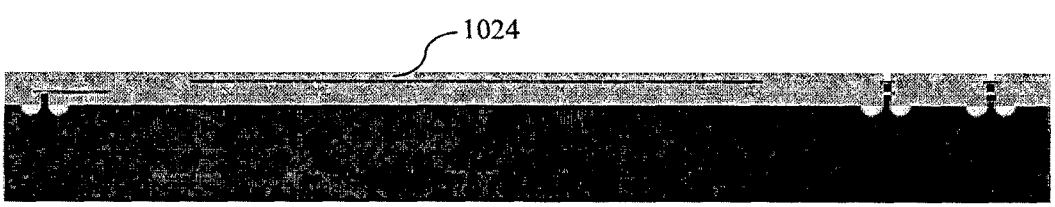
Figure 10K:
Figure 10L:
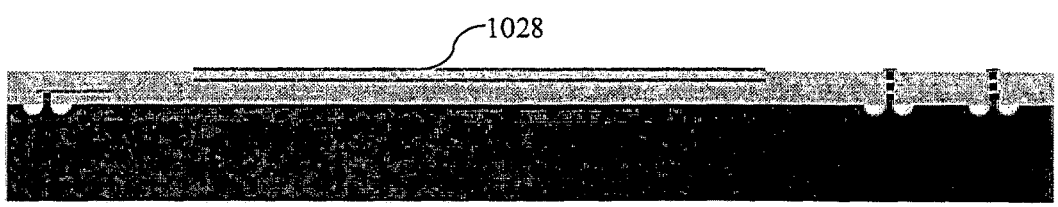
Figure 10M:
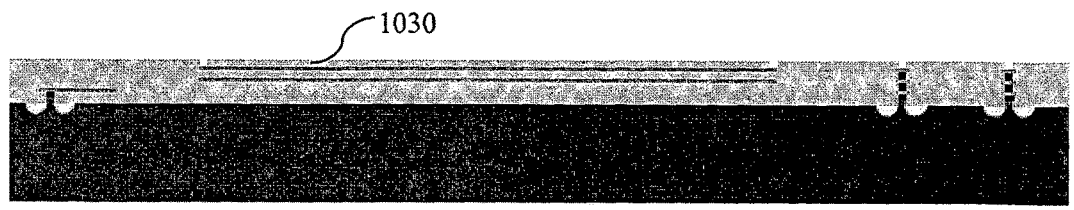
Figure 10N:
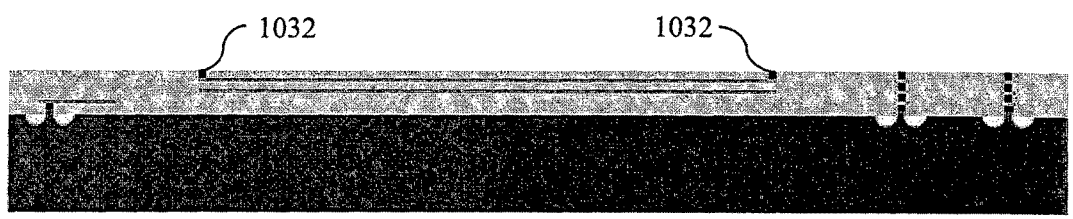
Figure 10O:
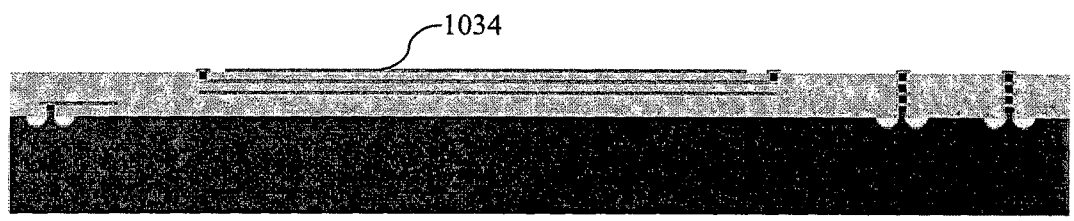
Figure 10P:
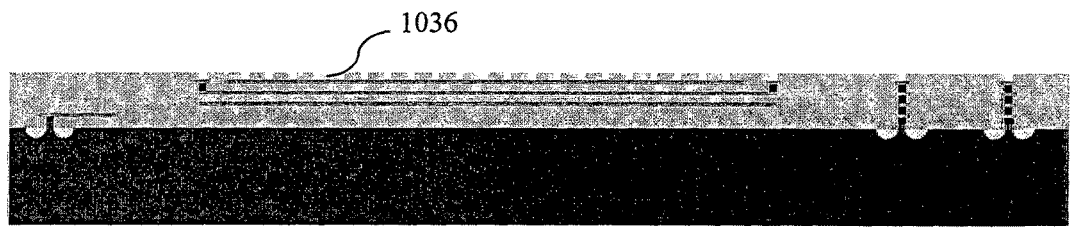
Figure 10Q:
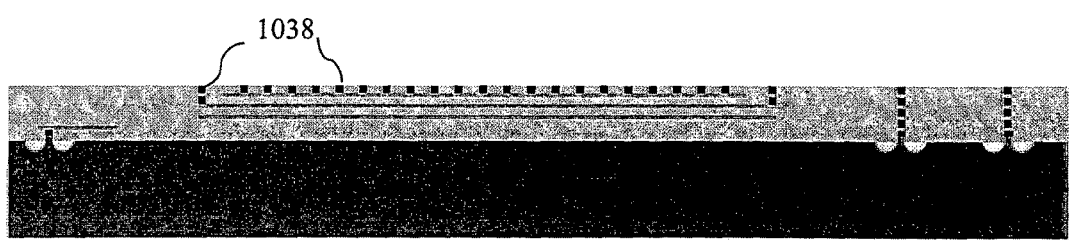
Figure 10R:
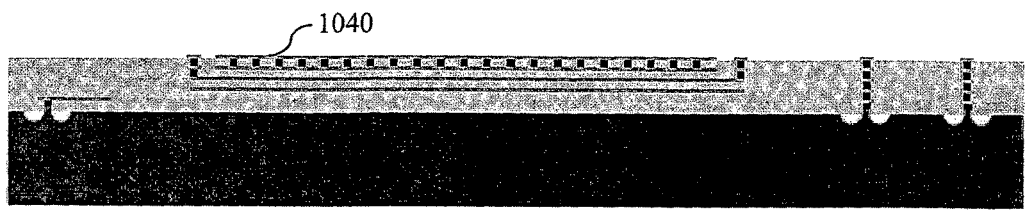

This metal layer 1022 will be utilised to define the bottom/stationary electrode 322 of the pressure sensor 120. Subsequently, the IMD2 (intra metal dielectric) layer 1024 is deposited over the METAL2 layer 1022 and the IMD1 layer 1018 and patterned as shown in FIG. 10J, and the VIA23 1026 is deposited and subjected to CMP as shown in FIG. 10K. The METAL3 layer 1028 is then deposited on the IMD2 layer 1024 and patterned as shown in FIG. 10L. This metal layer 1028 will be utilised to define the release layer of the pressure sensor 120 (i.e., to form the cavity 350 as shown in FIG. 3A). Subsequently, the IMD3 1030 is deposited over the METAL3 layer 1028 and patterned as shown in FIG. 10M, and then the VIA34 1032 is deposited and subjected to CMP as shown in FIG. 10N. The METAL4 layer 1034 is then deposited on the IMD3 layer 1030 and patterned as shown in FIG. 10O. This metal layer 1034 will be utilised to define the top/movable electrode 318 of the pressure sensor 120. Subsequently, the IMD4 layer 1036 is deposited on the METAL4 layer 1034 and patterned as shown in FIG. 10P, and then the VIA45 1038 is deposited and subjected to CMP as shown in FIG. 10Q. The METAL5 layer 1040 is then deposited on the IMD4 layer 1036 and patterned as shown in FIG. 10R. This metal layer 1040 will also be utilised to define the top/movable electrode 318 of the pressure sensor 120, connected in parallel with the METAL4 layer 1034.

Figure 10S:
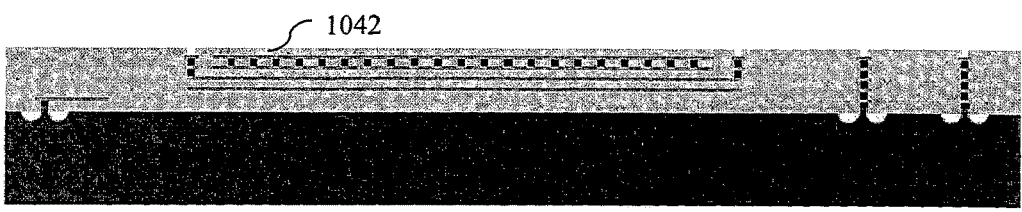
Figure 10T:
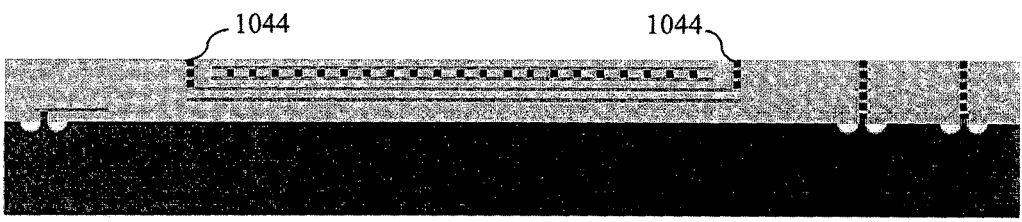
Figure 10U:
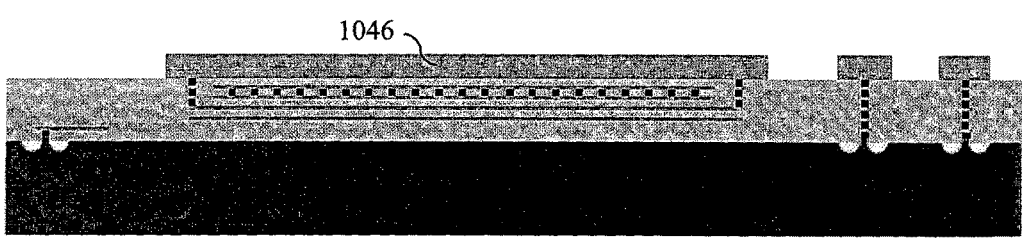
Figure 10V:
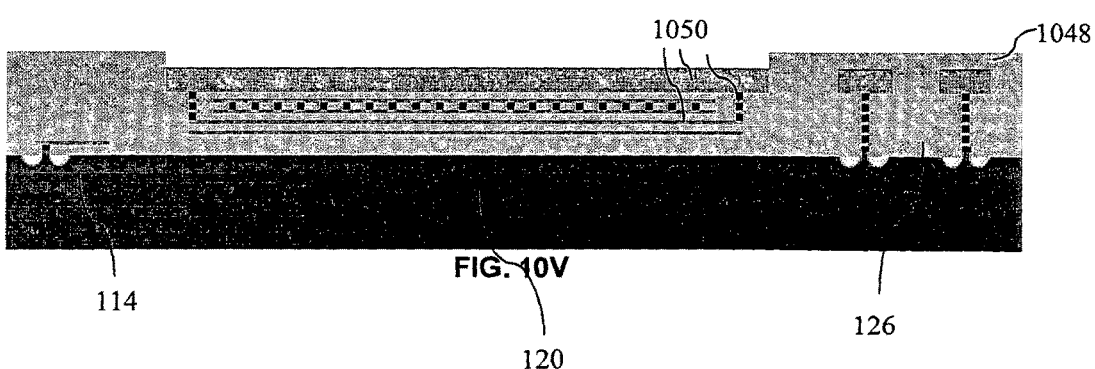

Subsequently, the IMD5 layer 1042 is deposited on the METAL5 layer 1040 and patterned as shown in FIG. 10S, and then the VIA56 1044 is deposited and subjected to CMP as shown in FIG. 10T. The METAL6 layer 1046 (i.e., the top metal layer 142) is then deposited on the IMD5 layer 1042 and patterned as shown in FIG. 10U. This metal layer 1046 will be utilised to fabricate the electrodes 410 of the oxygen sensor 126. Subsequently, a passivation oxide layer 1048 is deposited over the device and patterned as shown in FIG. 10V. It will be appreciated that routing to/from and within the ASIC 500 can be done using any metal layer described above.

Figure 10W:
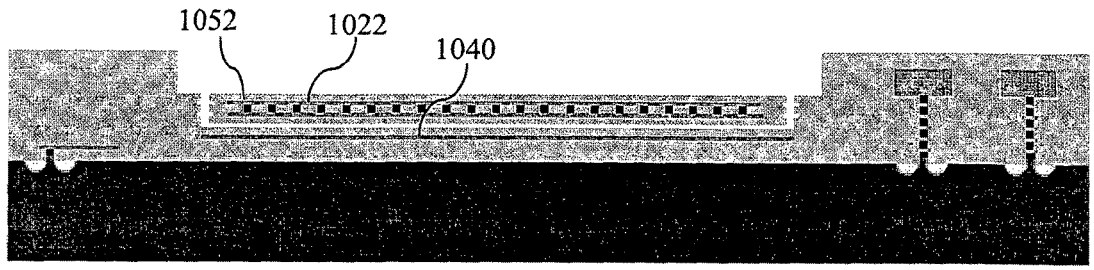
Figure 10X:
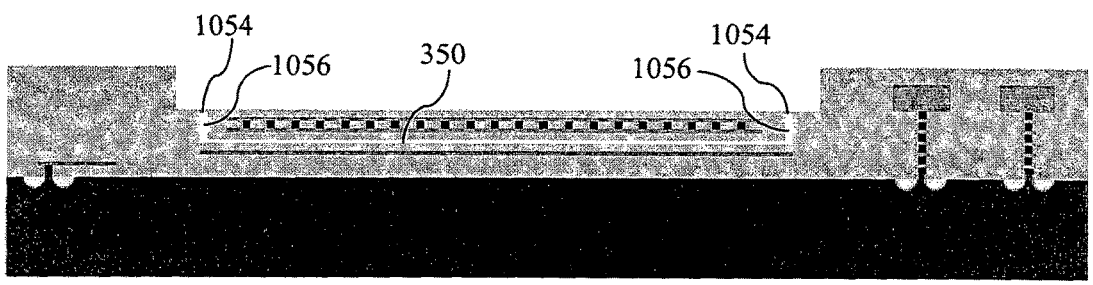
Figure 10Y:
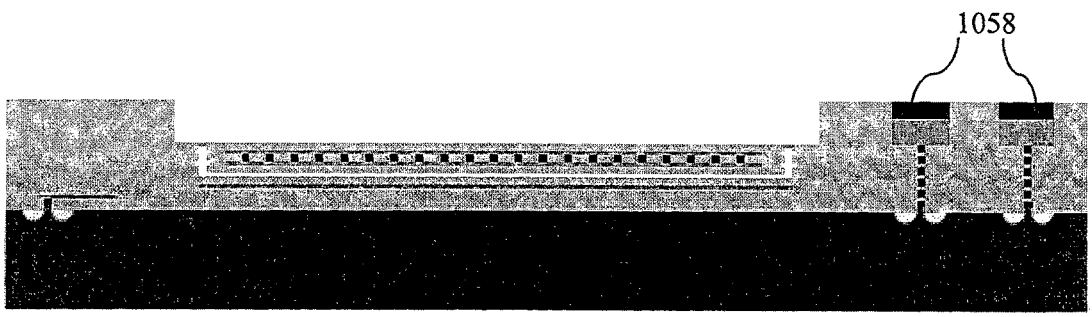
Figure 10Z:
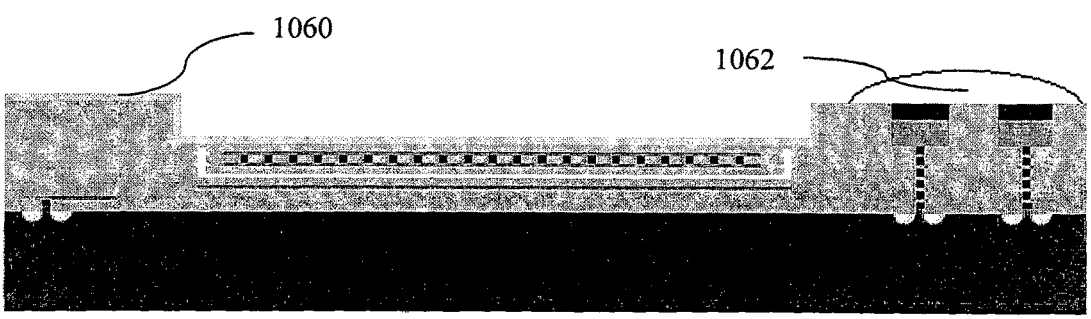

The CMOS wafer is now completed and the CMOS post-fabrication process will now be described. In order to ensure the CMOS compatibility, only low temperature post-process is used in the example embodiment. At this stage, the CMOS wafer have integrated thereon the temperature sensor 114, the pressure sensor 120 (but the membrane not yet released), and the oxygen sensor 120 (but without the platinum working electrode 410 deposited yet). In the post-fabrication process, a first step is to etch the sacrificial stacked layer 1050 in order to release the suspended membrane 1052 as shown in FIG. 10W. In order to etch the stacked metal (>99% Aluminium) and via (Tungsten) layers, a H2SO4+H2O2 solution is used to perform the release. During the etching of the sacrificial layer 1050, the dielectric acts as stopping layer protecting top electrode 1040 and bottom electrode 1022, electrical connections and IC, if required. After the release of the membrane 1052, low stress oxide layer 1054 is deposited in order to seal the etching holes 1056 as shown in FIG. 10X. The etching holes 1056 are sealed under a vacuum chamber, so the cavity 350 under the membrane 1052 is nearly in vacuum (about 6 mTorr). Subsequently, using photolithography and RIE the oxide layer 1054 is patterned in order to expose the oxygen sensor 126, and then Platinum 1058 is deposited on the top metal layer 1046 and patterned using a lift-off process to form the working electrodes 410 as shown in FIG. 10Y. In addition, using photolithography and RIE, the oxide layer 1054 is patterned in order to expose the pads (not shown in FIG. 10Z) to allow electrical connections. Once the CMOS-MEMS fabrication is finished, biocompatible packaging process is performed, including deposition and patterning of a protective polymer coating material (preferably Parylene) 1060 over the pressure sensor 120 and deposition of a polymer (preferably, hydrogel (NAFION)) 1062 to encapsulate the oxygen sensor 125 as shown in FIG. 10Z.

FIG. 11 illustrates an example completed sensor device (or sensor chip) 100 fabricated according to the example embodiment of the present invention.

Figure 12C:
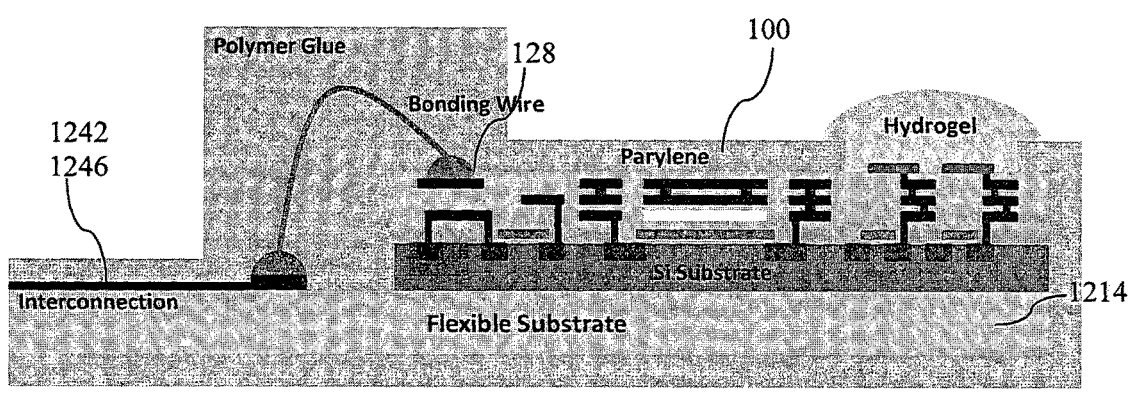
Figure 13:
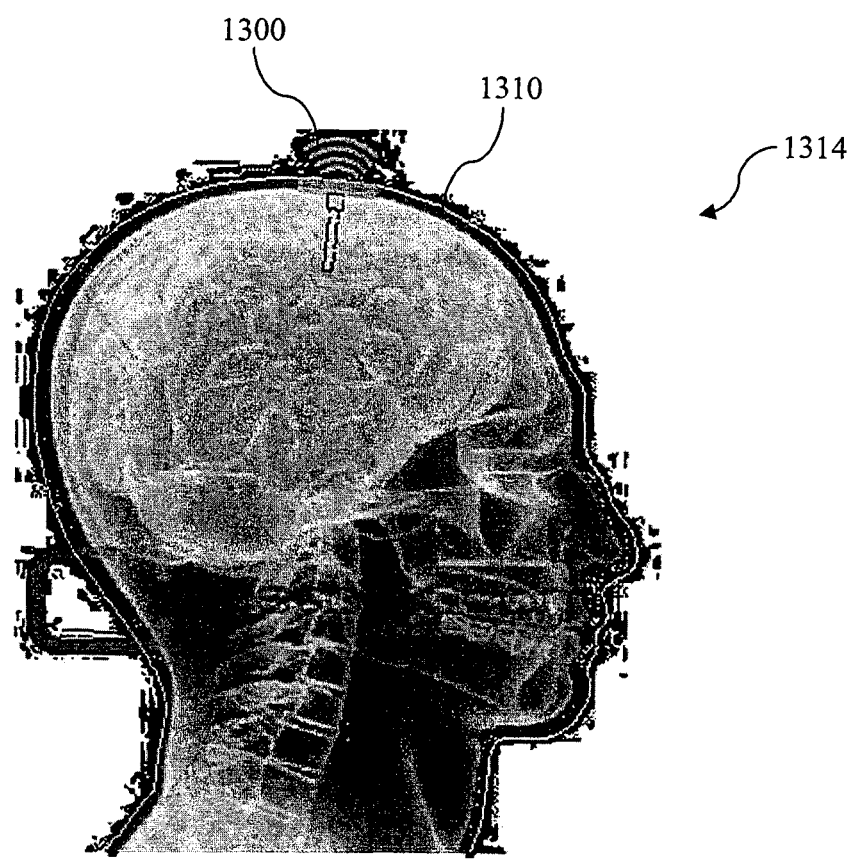
FIG. 13 depicts an example of the sensor system being used for in-vivo application.

An embodiment of the present invention will now be described where the sensor device 100 is packaged for in-vivo application as illustrated in FIG. 12A and FIG. 12B. In particular, there is provided an integrated multimodal sensor system 1200 for intracranial neuromonitoring as schematically depicted in FIG. 12A incorporating the sensor device 100. The sensor system 1200 comprises a flexible catheter 1210, a flexible substrate 1214, a sensor device 100 disposed on the flexible substrate 1214 and within a sensing end portion 1222 of the flexible catheter 1210, and a guide tip member 1226 extending from the sensing end portion 1222 of the flexible catheter 1210 to facilitate penetration and directional guidance of the flexible catheter 1210 during insertion of the sensing end portion 1222 of the flexible catheter 1210 into the skull/cranium 1310 of a subject 1314 as illustrated in FIG. 13. In the example embodiment, the sensor device 100 is glued onto a flexible substrate 1214 (e.g., flexible PCB) which is biocompatible. The soft nature of the flexible substrate 1214 minimises the possibility of disrupting the tissue, but it has been found to suffer from directional guidance. Accordingly, in the example embodiment, the guide tip member 1226 is assembled adjacent the sensor device 100 to provide facilitate penetration and directional guidance of the flexible catheter 1210 into the skull 1310. Preferably, the guide tip member 1226 has a rounded tip and is made of silicone.

In the example embodiment, the sensor system 1200 further comprises a housing 1230 including a wireless communication module 1234 for receiving sensed data from the sensor device 100 and an antenna module 1236 for transmitting the sensed data wirelessly to one or more remote extracranial devices (e.g., a computer which receives the transmitted data and stores and/or displays the received data). The housing 1230 may further comprise a power source 1238, such as a battery, for powering the sensor system 1200. The power source 1238 and the wireless communication module 1234 are installed on a PCB 1240 of the housing 1230. As illustrated in FIG. 12A, the flexible catheter 1218 has a power wire 1242 and a signal wire 1246 therein each extending between and connected to the sensor device 100 and the housing 1230 (i.e., the PCB 1240). The power wire 1242 is arranged to supply power from the power source 1238 to the sensor device 100 and the signal wire 1246 is arranged to transmit the sensed data from the sensor device 100 to the wireless communication module 1234. In this regard, the sensor device 100 comprises a plurality of contacts 128 (or I/O ports) which is configured to be bonded to the power wire 1242 and the signal wire 1246 in the sensor system 1200. FIG. 12C illustrates the same sensor device 100 as FIG. 1B but the power wire 1242 and signal wire(s) 1246 connected to the contacts 128 via bonding wires (only one bonding wire is shown in FIG. 12C). By way of example only, there are 8 contacts 128 for connecting to 8 bonding wires. As can be appreciated from FIG. 11, the contacts 128 are advantageously arranged so as to allow single-side wirebonding.

The sensor system 1200 also comprises a fastener (e.g., bolt) 1250 formed on a bottom side of the housing 1230 for attaching the housing 1230 to the skull 1210 of the subject 1214, and thus supporting the flexible catheter 1210 and the sensor device 100 within the skull 1210 for intracranial neuromonitoring. As shown in FIG. 11A, the flexible catheter 1210 attached to and extending from the housing 1230 may run through a central hollow portion of the fastener 1250.

By way of example only, FIG. 12B illustrates a prototype of the flexible catheter 1210 with the sensor device 100 embedded therein, along with the guide tip member 1226 extending from the sensor device 100.

Figure 14:
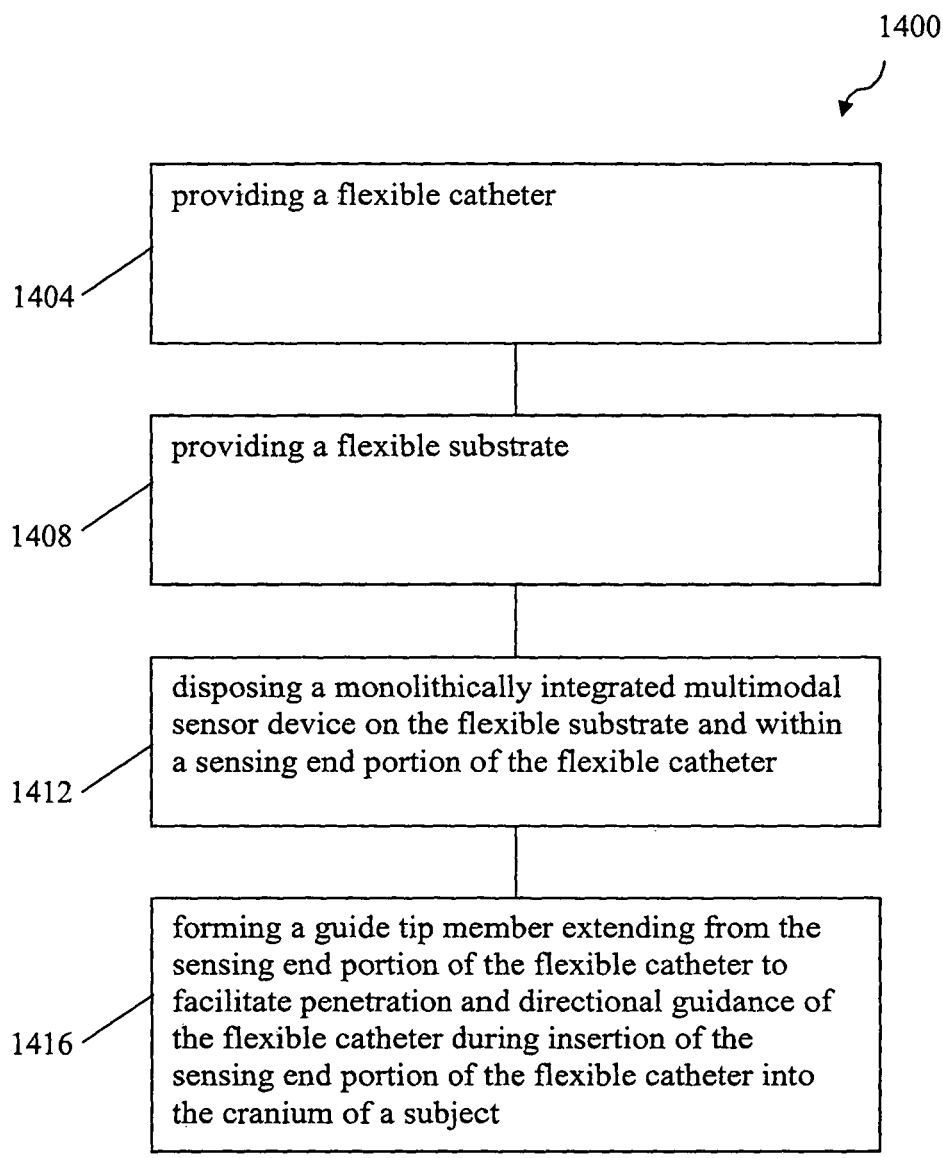
FIG. 14 depicts an overview of a method of fabricating the sensor system for intracranial neuromonitoring according to an embodiment of the present invention.

An overview of a method 1400 of fabricating the sensor system 1200 for intracranial neuromonitoring will now be described according to an embodiment of the present invention with reference to FIG. 14. The method 1400 comprises a step 1404 of providing a flexible catheter 1210, a step 1408 of providing a flexible substrate 1214, a step 1412 of disposing a sensor device 100 on the flexible substrate 1214 and within a sensing end portion 1222 of the flexible catheter 1210, and a step 1416 of forming a guide tip member 1226 extending from the sensing end portion 1222 of the flexible catheter 1210 to facilitate penetration and directional guidance of the flexible catheter 1210 during insertion of the sensing end portion 1222 of the flexible catheter 1210 into the cranium 1310 of a subject 1314.

Figure 15:
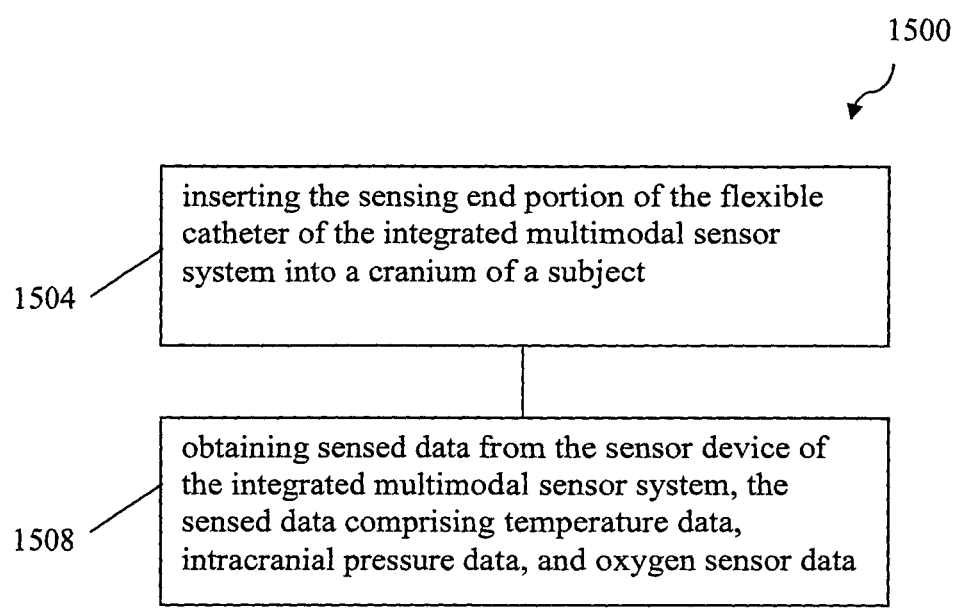
FIG. 15 depicts an overview of a method of intracranial neuromonitoring using the integrated multimodal sensor system for in-vivo application according to an embodiment of the present invention.

An overview of a method 1500 of intracranial neuromonitoring using the integrated multimodal sensor system for in-vivo application will now be generally described with reference to FIG. 15. The method 1500 comprises a step 1504 of inserting the sensing end portion 1222 of the flexible catheter 1210 of the integrated multimodal sensor system 1200 into a cranium 1310 of a subject 1314 and a step 1508 of obtaining sensed data from the sensor device 100 of the integrated multimodal sensor system 1200, the sensed data comprising temperature data, intracranial pressure data, and oxygen sensor data.

Accordingly, example embodiments of the present invention described herein provide a monolithically integrated multimodal sensor device 100 for intracranial neuromonitoring, including a temperature sensor for detecting intracranial temperature, a pressure sensor for detecting intracranial pressure, and an oxygen sensor for detecting oxygen concentration. In particular, the temperature sensor, the pressure sensor, and the oxygen sensor are integrated on a single substrate. This advantageously enables the sensor device having intracranial temperature, intracranial pressure and oxygen concentration sensing capabilities to be provided with a single catheter, thus eliminating the need to provide multiple catheters for obtaining multiple physiologic parameters. In addition, the sensor device 100 can advantageously be fabricated in a CMOS-compatible process, thus reducing fabrication costs. The miniaturized size of the sensor device facilitates the integration of full intracranial neuromonitoring system 1200 in a single catheter 1210. As a result, the size of the bolt or burr hole required to perform intracranial neuromonitoring can be minimised, thus making it less susceptible to bleeding and infection. The overall intracranial neuromonitoring process is also greatly simplified since, for example, less catheters are involved.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

What is claimed is:

1. A monolithically integrated multimodal sensor device for intracranial neuromonitoring, the sensor device comprising:
   a single substrate;
   a temperature sensor formed on a first portion of the single substrate for detecting temperature;
   a pressure sensor formed on a second portion of the single substrate for detecting intracranial pressure; and
   an oxygen sensor formed on a third portion of the single substrate for detecting oxygen concentration,
   wherein the temperature sensor, the pressure sensor, and the oxygen sensor are formed on the single substrate such that sensing portions of the temperature sensor, the oxygen sensor, and the pressure sensor, respectively, are formed at different layers of the sensor device as seen from a cross-sectional side view of the sensor device, and
   wherein the sensing portion of the temperature sensor is formed at a top of the single substrate as seen from the cross-sectional side view, the sensing portion of the pressure sensor being formed at intra-metal layers of the sensor device that exist between the top of the single substrate and a top of the sensor device as seen from the cross-sectional side view, and the sensing portion of the oxygen sensor being formed at a top metal layer of the sensor device that is above both the sensing portions of the temperature sensor and the pressure sensor as seen from the cross-sectional side view.

2. The sensor device according to claim 1, wherein the temperature sensor comprises one or more transistors, and the sensing portion of the temperature sensor includes an active region of the respective one or more transistors.

3. The sensor device according to claim 2, wherein the transistor is a parasitic vertical PNP transistor.

4. The sensor device according to claim 1, wherein the pressure sensor comprises one or more capacitive MEMS pressure sensors, and the sensing portion of the pressure sensor includes a movable electrode of the respective one or more capacitive MEMS pressure sensors.

5. The sensor device according to claim 1, wherein the oxygen sensor comprises a switchable array of oxygen sensor elements, and the sensing portion of the oxygen sensor comprises a working electrode of the respective oxygen sensor elements.

6. The sensor device according to claim 5, wherein the oxygen sensor is configured to switch to one of the oxygen sensor elements to provide the oxygen level reading which satisfies a predetermined sensitivity level.

7. The sensor device according to claim 1, further comprises one or more application-specific integrated circuits formed on the single substrate for processing readings from the temperature sensor, the oxygen sensor, and the oxygen sensor.

8. A method of fabricating a monolithically integrated multimodal sensor device for intracranial neuromonitoring, the method comprising:
   providing a single substrate;
   fabricating, on a first portion of the single substrate, a temperature sensor that detects temperature;
   fabricating, on a second portion of the single substrate, a pressure sensor that detects intracranial pressure; and
   fabricating, on a third portion of the single substrate, an oxygen sensor that detects oxygen concentration,
   wherein the temperature sensor, the pressure sensor, and the oxygen sensor are formed on the single substrate such that sensing portions of the temperature sensor, the oxygen sensor, and the pressure sensor, respectively, are each formed at different layers of the sensor device as seen from a cross-sectional side view of the sensor device, and wherein the sensing portion of the temperature sensor is formed at a top of the single substrate as seen from the cross-sectional side view, the sensing portion of the pressure sensor being formed at intra-metal layers of the sensor device that exist between the top of the single substrate and a top of the sensor device as seen from the cross-sectional side view, and the sensing portion of the oxygen sensor being formed at a top metal layer of the sensor device that is above both the sensing portions of the temperature sensor and pressure sensor as seen from the cross-sectional side view.

9. The method according to claim 8, wherein the temperature sensor comprises one or more transistors, and the sensing portion of the temperature sensor includes an active region of the respective one or more transistors.

10. The method according to claim 9, wherein the transistor is a parasitic vertical PNP transistor.

11. The method according to claim 8, wherein the pressure sensor comprises one or more capacitive MEMS pressure sensors, and the sensing portion of the pressure sensor includes a movable electrode of the respective one or more capacitive MEMS pressure sensors.

12. The method according to claim 8, wherein the oxygen sensor comprises a switchable array of oxygen sensor elements, and the sensing portion of the oxygen sensor comprises a working electrode of the respective oxygen sensor elements.

13. The method according to claim 12, wherein the oxygen sensor is configured to switch to one of the oxygen sensor elements to provide the oxygen level reading which satisfies a predetermined sensitivity level.

14. The method according to claim 8, further comprises forming one or more application-specific integrated circuits on the single substrate for processing readings from the temperature sensor, the oxygen sensor, and the oxygen sensor.

15. An integrated multimodal sensor system for intracranial neuromonitoring, the sensor system comprising:
a flexible catheter;
a flexible substrate;
a monolithically integrated multimodal sensor device for intracranial neuromonitoring, the sensor comprising:
a single substrate;
a temperature sensor formed on a first portion of the single substrate for detecting temperature;
a pressure sensor formed on a second portion of the single substrate for detecting intracranial pressure; and
an oxygen sensor formed on a third portion of the single substrate for detecting oxygen concentration,
wherein the temperature sensor, the pressure sensor, and the oxygen sensor are formed on the single substrate such that sensing portions of the temperature sensor, the oxygen sensor, and the pressure sensor, respectively, are formed at different layers of the sensor device as seen from a cross-sectional side view of the sensor device, wherein the monolithically integrated multimodal sensor device is disposed on the flexible substrate and within a sensing end portion of the flexible catheter, and wherein the sensing portion of the temperature sensor is formed at a top of the single substrate as seen from the cross-sectional side view, the sensing portion of the pressure sensor being formed at intra-metal layers of the sensor device that exist between the top of the single substrate and a top of the sensor device as seen from the cross-sectional side view, and the sensing portion of the oxygen sensor being formed at a top metal layer of the sensor device that is above both the sensing portions of the temperature sensor and the pressure sensor as seen from the cross-sectional side view; and a guide tip member extending from the sensing end portion of the flexible catheter to facilitate penetration and directional guidance of the flexible catheter during insertion of the sensing end portion of the flexible catheter into the cranium.

16. The integrated multimodal sensor system according to claim 15, wherein the guide tip member has a rounded tip and is made of silicone.

17. The integrated multimodal sensor system according to claim 16, further comprising a housing including therein a wireless communication module for receiving sensed data from the sensor device and an antenna for transmitting the sensed data wirelessly to one or more remote extracranial devices.

18. A method of forming an integrated multimodal sensor system for intracranial neuromonitoring, the method comprising:
providing a flexible catheter;
providing a flexible substrate;
disposing a monolithically integrated multimodal sensor device on the flexible substrate and within a sensing end portion of the flexible catheter, wherein the sensor device comprises:
a single substrate;
a temperature sensor that detects temperature and that is formed on a first portion of the single substrate;
a pressure sensor that detects intracranial pressure and that is formed on a second portion of the single substrate; and
an oxygen sensor that detects oxygen concentration and that is formed on a third portion of the single substrate,
wherein the temperature sensor, the pressure sensor, and the oxygen sensor are formed on the single substrate such that sensing portions of the temperature sensor, the oxygen sensor, and the pressure sensor, respectively, are formed at different layers of the sensor device as seen from a cross-sectional side view of the sensor device, and wherein the sensing portion of the temperature sensor is formed at a top of the single substrate as seen from the cross-sectional side view, the sensing portion of the pressure sensor being formed at intra-metal layers of the sensor device that exist between the top of the single substrate and a top of the sensor device as seen from the cross-sectional side view, and the sensing portion of the oxygen sensor being formed at a top metal layer of the sensor device that is above both the sensing portions of the temperature sensor and pressure sensor as seen from the cross-sectional side view; and
fabricating a guide tip member that extends from the sensing end portion of the flexible catheter.

* * * * *